US011401550B2

(12) United States Patent
Weitz et al.

(10) Patent No.: US 11,401,550 B2
(45) Date of Patent: Aug. 2, 2022

(54) CREATION OF LIBRARIES OF DROPLETS AND RELATED SPECIES

(71) Applicant: President and Fellows of Harvard College, Cambridge, MA (US)

(72) Inventors: David A. Weitz, Bolton, MA (US); Jeremy Agresti, Richmond, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 350 days.

(21) Appl. No.: 14/812,951

(22) Filed: Jul. 29, 2015

(65) Prior Publication Data
US 2015/0336071 A1 Nov. 26, 2015

Related U.S. Application Data

(63) Continuation of application No. 13/119,470, filed as application No. PCT/US2009/005184 on Sep. 17, 2009, now abandoned.

(60) Provisional application No. 61/098,674, filed on Sep. 19, 2008.

(51) Int. Cl.
| | | |
|---|---|---|
| *B01J 19/00* | (2006.01) | |
| *C12Q 1/68* | (2018.01) | |
| *C12Q 1/6876* | (2018.01) | |
| *C12Q 1/6874* | (2018.01) | |
| *B01J 13/04* | (2006.01) | |

(52) U.S. Cl.
CPC ............ *C12Q 1/6876* (2013.01); *B01J 13/04* (2013.01); *B01J 19/0046* (2013.01); *C12Q 1/6874* (2013.01); *B01J 2219/00599* (2013.01); *B01J 2219/00709* (2013.01); *B01J 2219/00711* (2013.01); *B01J 2219/00716* (2013.01); *B01J 2219/00722* (2013.01)

(58) Field of Classification Search
CPC ........ B01J 19/0046; B01J 2219/00599; C12Q 1/6876; C12Q 1/6874
See application file for complete search history.

(56) References Cited

U.S. PATENT DOCUMENTS

| | | |
|---|---|---|
| 4,732,930 A | 3/1988 | Tanaka et al. |
| 4,743,507 A | 5/1988 | Franses et al. |
| 4,996,265 A | 2/1991 | Okubo et al. |
| 5,055,390 A | 10/1991 | Weaver et al. |
| 5,100,933 A | 3/1992 | Tanaka et al. |
| 5,120,349 A | 6/1992 | Stewart et al. |
| 5,149,625 A | 9/1992 | Church et al. |
| 5,202,231 A | 4/1993 | Drmanac et al. |
| 5,216,096 A | 6/1993 | Hattori et al. |
| 5,326,692 A | 7/1994 | Brinkley et al. |
| 5,436,130 A | 7/1995 | Mathies et al. |
| 5,500,223 A | 3/1996 | Behan et al. |
| 5,512,131 A | 4/1996 | Kumar et al. |
| 5,695,940 A | 12/1997 | Drmanac et al. |
| 5,736,330 A | 4/1998 | Fulton |
| 5,834,252 A | 11/1998 | Stemmer et al. |
| 5,849,055 A | 12/1998 | Arai et al. |
| 5,851,769 A | 12/1998 | Gray et al. |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,297,006 B1 | 10/2001 | Drmanac et al. |
| 6,297,017 B1 | 10/2001 | Schmidt et al. |
| 6,355,198 B1 | 3/2002 | Kim et al. |
| 6,361,950 B1 | 3/2002 | Mandecki |
| 6,380,297 B1 | 4/2002 | Zion et al. |
| 6,432,360 B1 | 8/2002 | Church |
| 6,485,944 B1 | 11/2002 | Church et al. |
| 6,500,447 B1 | 12/2002 | Dexter et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,058 B2 | 10/2004 | Jesperson et al. |
| 6,913,935 B1 | 7/2005 | Thomas |
| 6,929,859 B2 | 8/2005 | Chandler et al. |
| 7,041,481 B2 | 5/2006 | Anderson et al. |
| 7,268,167 B2 | 9/2007 | Higuchi et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,638,276 B2 | 12/2009 | Griffiths et al. |
| 7,708,949 B2 | 5/2010 | Stone et al. |
| 7,776,927 B2 | 8/2010 | Chu et al. |
| RE41,780 E | 9/2010 | Anderson et al. |
| 7,799,553 B2 | 9/2010 | Mathies et al. |
| 7,968,287 B2 | 6/2011 | Griffiths et al. |
| 8,252,539 B2 | 8/2012 | Quake et al. |

(Continued)

FOREIGN PATENT DOCUMENTS

| | | |
|---|---|---|
| CN | 1150764 A | 5/1997 |
| EP | 0 249 007 A2 | 12/1987 |

(Continued)

OTHER PUBLICATIONS

Invitation to Pay Additional Fees for PCT/US2008/003185 dated Oct. 22, 2008.

(Continued)

*Primary Examiner* — Sahana S Kaup
(74) *Attorney, Agent, or Firm* — Wolf, Greenfield & Sacks, P.C.

(57) ABSTRACT

The present invention is generally related to systems and methods for producing a plurality of droplets. The droplets may contain varying species, e.g., for use as a library. In some cases, the fluidic droplets may be rigidified to form rigidified droplets (e.g., gel droplets). In certain embodiments, the droplets may undergo a phase change (e.g., from rigidified droplets to fluidized droplets), as discussed more herein. In some cases, a species may be added internally to a droplet by exposing the droplet to a fluid comprising a plurality of species.

23 Claims, 9 Drawing Sheets

(56) References Cited

U.S. PATENT DOCUMENTS

| | | |
|---|---|---|
| 8,273,573 B2 | 9/2012 | Ismagilov et al. |
| 8,278,071 B2 | 10/2012 | Brown et al. |
| 8,329,407 B2 | 12/2012 | Ismagilov et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,871,444 B2 | 10/2014 | Griffiths et al. |
| 9,017,948 B2 | 4/2015 | Agresti et al. |
| 9,029,085 B2 | 5/2015 | Agresti et al. |
| 9,039,273 B2 | 5/2015 | Weitz et al. |
| 9,068,210 B2 | 6/2015 | Agresti et al. |
| 9,689,024 B2 | 6/2017 | Hindson et al. |
| 9,816,121 B2 | 6/2017 | Agresti et al. |
| 9,695,468 B2 | 7/2017 | Hindson et al. |
| 9,718,044 B2 | 8/2017 | Wesner et al. |
| 9,850,526 B2 | 12/2017 | Agresti et al. |
| 9,856,530 B2 | 1/2018 | Hindson et al. |
| 10,221,437 B2 * | 3/2019 | Weitz .................. C12Q 1/6848 |
| 10,471,016 B2 | 11/2019 | Weitz et al. |
| 10,508,294 B2 * | 12/2019 | Weitz .................. B01F 13/0062 |
| 10,683,524 B2 * | 6/2020 | Weitz .................. C12Q 1/6834 |
| 10,738,337 B2 | 8/2020 | Weitz et al. |
| 10,941,430 B2 | 3/2021 | Weitz et al. |
| 11,123,297 B2 | 9/2021 | Weitz et al. |
| 2001/0020588 A1 | 9/2001 | Adourian et al. |
| 2001/0044109 A1 | 11/2001 | Mandecki |
| 2002/0034737 A1 * | 3/2002 | Drmanac .................. C12Q 1/6874 435/6.12 |
| 2002/0034747 A1 | 3/2002 | Bruchez et al. |
| 2002/0051992 A1 | 5/2002 | Bridgham et al. |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0099954 A1 | 5/2003 | Miltenyi et al. |
| 2003/0104466 A1 | 6/2003 | Knapp et al. |
| 2003/0108897 A1 | 6/2003 | Drmanac |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0096515 A1 | 5/2004 | Bausch et al. |
| 2004/0132122 A1 | 7/2004 | Banerjee et al. |
| 2004/0253613 A1 * | 12/2004 | Taylor .................. B01J 19/0046 435/6.11 |
| 2005/0019839 A1 | 1/2005 | Jesperson et al. |
| 2005/0042625 A1 | 2/2005 | Schmidt et al. |
| 2005/0123614 A1 | 6/2005 | Kim et al. |
| 2005/0136486 A1 | 6/2005 | Haushalter |
| 2005/0172476 A1 | 8/2005 | Stone et al. |
| 2005/0181379 A1 | 8/2005 | Su et al. |
| 2005/0202429 A1 * | 9/2005 | Trau .................. B01J 13/02 435/6.16 |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0078893 A1 | 4/2006 | Griffiths et al. |
| 2006/0153924 A1 | 7/2006 | Griffiths et al. |
| 2006/0163385 A1 | 7/2006 | Link et al. |
| 2006/0240506 A1 | 10/2006 | Kushmaro et al. |
| 2006/0257893 A1 | 11/2006 | Takahashi et al. |
| 2006/0292583 A1 | 12/2006 | Schneider et al. |
| 2007/0003442 A1 | 1/2007 | Link et al. |
| 2007/0020617 A1 * | 1/2007 | Trnovsky .................. C12Q 1/68 435/5 |
| 2007/0054119 A1 | 3/2007 | Garstecki et al. |
| 2007/0092914 A1 | 4/2007 | Griffiths et al. |
| 2007/0172827 A1 | 7/2007 | Murakami |
| 2007/0172873 A1 | 7/2007 | Brenner et al. |
| 2007/0195127 A1 * | 8/2007 | Ahn .................. B01F 13/0071 347/55 |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2009/0012187 A1 | 1/2009 | Chu et al. |
| 2009/0035770 A1 | 2/2009 | Mathies et al. |
| 2009/0068170 A1 | 3/2009 | Weitz et al. |
| 2009/0131543 A1 | 5/2009 | Weitz et al. |
| 2009/0134027 A1 * | 5/2009 | Jary .................. F15C 5/00 204/450 |
| 2009/0191276 A1 | 7/2009 | Kim et al. |
| 2009/0197772 A1 | 8/2009 | Griffiths et al. |
| 2009/0286687 A1 | 11/2009 | Dressman et al. |
| 2010/0022414 A1 | 1/2010 | Link et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2010/0213628 A1 | 8/2010 | Bausch et al. |
| 2010/0273219 A1 | 10/2010 | May et al. |
| 2011/0033854 A1 | 2/2011 | Drmanac et al. |
| 2011/0086780 A1 | 4/2011 | Colston et al. |
| 2011/0092392 A1 | 4/2011 | Colston et al. |
| 2011/0160078 A1 | 6/2011 | Fodor et al. |
| 2011/0218123 A1 | 9/2011 | Weitz et al. |
| 2011/0229545 A1 | 9/2011 | Shum et al. |
| 2011/0267457 A1 | 11/2011 | Weitz et al. |
| 2011/0305761 A1 | 12/2011 | Shum et al. |
| 2012/0003321 A1 | 1/2012 | Peng et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0076860 A1 | 3/2012 | Trout et al. |
| 2012/0135407 A1 | 5/2012 | Slatter |
| 2012/0190032 A1 | 7/2012 | Ness et al. |
| 2012/0199226 A1 | 8/2012 | Weitz et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0004522 A1 | 1/2013 | Taylor et al. |
| 2013/0046030 A1 | 2/2013 | Rotem et al. |
| 2013/0064862 A1 | 3/2013 | Weitz et al. |
| 2013/0079231 A1 | 3/2013 | Pushkarev et al. |
| 2013/0109575 A1 | 5/2013 | Kleinschmidt et al. |
| 2013/0157899 A1 | 6/2013 | Adler et al. |
| 2013/0210639 A1 | 8/2013 | Link et al. |
| 2013/0274117 A1 | 10/2013 | Church et al. |
| 2014/0065234 A1 | 3/2014 | Shum et al. |
| 2014/0155295 A1 | 6/2014 | Hindson et al. |
| 2014/0199730 A1 | 7/2014 | Agresti et al. |
| 2014/0199731 A1 | 7/2014 | Agresti et al. |
| 2014/0220350 A1 | 8/2014 | Kim et al. |
| 2014/0227684 A1 | 8/2014 | Hindson et al. |
| 2014/0235506 A1 | 8/2014 | Hindson et al. |
| 2014/0303039 A1 | 10/2014 | Weitz et al. |
| 2014/0378349 A1 | 12/2014 | Hindson et al. |
| 2015/0005200 A1 | 1/2015 | Hindson et al. |
| 2015/0314292 A1 | 11/2015 | Weitz et al. |
| 2015/0336068 A1 | 11/2015 | Weitz et al. |
| 2015/0336069 A1 | 11/2015 | Weitz et al. |
| 2015/0336070 A1 | 11/2015 | Weitz et al. |
| 2015/0336071 A1 | 11/2015 | Weitz et al. |
| 2015/0336072 A1 | 11/2015 | Weitz et al. |
| 2015/0337371 A1 | 11/2015 | Weitz et al. |
| 2015/0353999 A1 | 12/2015 | Agresti et al. |
| 2016/0279068 A1 | 9/2016 | Utech et al. |
| 2017/0183701 A1 | 6/2017 | Agresti et al. |
| 2017/0224849 A1 | 8/2017 | Carroll et al. |
| 2017/0319443 A1 | 12/2017 | Weitz et al. |
| 2018/0023109 A1 | 1/2018 | Weitz et al. |
| 2018/0119212 A1 | 5/2018 | Weitz et al. |
| 2018/0171373 A1 | 6/2018 | Weitz et al. |

(56) References Cited

U.S. PATENT DOCUMENTS

| | | | |
|---|---|---|---|
| 2018/0214385 | A1 | 8/2018 | Weitz et al. |
| 2018/0296488 | A1 | 10/2018 | Weitz et al. |
| 2020/0000274 | A1 | 1/2020 | Weitz et al. |
| 2020/0085753 | A1 | 3/2020 | Weitz et al. |
| 2020/0157593 | A1 | 5/2020 | Weitz et al. |
| 2020/0197894 | A1 | 6/2020 | Weitz et al. |
| 2021/0348203 | A1 | 11/2021 | Weitz et al. |

FOREIGN PATENT DOCUMENTS

| | | |
|---|---|---|
| EP | 0 272 659 A2 | 6/1988 |
| EP | 0 478 326 A1 | 4/1992 |
| EP | 1 019 496 B1 | 9/2004 |
| EP | 1 482 036 B1 | 10/2007 |
| EP | 1 594 980 B1 | 11/2009 |
| EP | 1 967 592 B1 | 4/2010 |
| EP | 2 258 846 A2 | 12/2010 |
| EP | 2 145 955 B1 | 2/2012 |
| EP | 1 905 828 B1 | 8/2012 |
| EP | 1 908 832 B1 | 12/2012 |
| EP | 2 540 389 A1 | 1/2013 |
| JP | S59-049832 A2 | 3/1984 |
| JP | 2004-361291 A | 12/2004 |
| JP | 2006-507921 A | 3/2006 |
| JP | 2006-289250 A | 10/2006 |
| JP | 2007-268350 A | 10/2007 |
| JP | 2007-298327 A | 11/2007 |
| JP | 2009-208074 A2 | 9/2009 |
| KR | 2014/0107381 A | 9/2014 |
| WO | WO 95/09613 A1 | 4/1995 |
| WO | WO 96/29629 A2 | 9/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO 01/14589 A2 | 3/2001 |
| WO | WO 01/85138 A2 | 11/2001 |
| WO | WO 01/89787 A2 | 11/2001 |
| WO | WO 02/31203 A2 | 4/2002 |
| WO | WO 02/047665 A2 | 6/2002 |
| WO | WO 02/086148 A1 | 10/2002 |
| WO | WO 03/028653 A1 | 4/2003 |
| WO | WO 2004/002627 A2 | 1/2004 |
| WO | WO 2004/091763 A2 | 10/2004 |
| WO | WO 2004/102204 A1 | 11/2004 |
| WO | WO 2004/103565 A2 | 12/2004 |
| WO | WO 2004/105734 A1 | 12/2004 |
| WO | WO 2005/021151 A1 | 3/2005 |
| WO | WO 2005/040406 A1 | 5/2005 |
| WO | WO2005041884 * | 5/2005 |
| WO | WO 2005/049787 A2 | 6/2005 |
| WO | WO 2005/082098 A2 | 9/2005 |
| WO | WO 2005/084210 A2 | 9/2005 |
| WO | WO 2005/103106 A1 | 11/2005 |
| WO | WO 2006/078841 A1 | 7/2006 |
| WO | WO 2006/096571 A2 | 9/2006 |
| WO | WO2006096571 * | 9/2006 |
| WO | WO 2007/001448 A2 | 1/2007 |
| WO | WO 2007/002490 A2 | 1/2007 |
| WO | WO-2007012638 A1 * 2/2007 ................ F15C 5/00 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO-2007092538 A2 * 8/2007 ........... C12Q 1/6813 |
| WO | WO 2007/114794 A1 | 10/2007 |
| WO | WO 2007/121489 A2 | 10/2007 |
| WO | WO 2007/133710 A2 | 11/2007 |
| WO | WO 2007/133807 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO-2007140015 A2 * 12/2007 ........ B01L 3/502784 |
| WO | WO 2008/021123 A1 | 2/2008 |
| WO | WO 2008/058297 A2 | 5/2008 |
| WO | WO 2008/091792 A2 | 7/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/005680 A1 | 1/2009 |
| WO | WO 2009/011808 A1 | 1/2009 |
| WO | WO 2009/085215 A1 | 7/2009 |
| WO | WO 2009/120254 A1 | 10/2009 |
| WO | WO 2009/148598 A1 | 12/2009 |
| WO | WO 2010/104604 A1 | 9/2010 |
| WO | WO 2010/151776 A2 | 12/2010 |
| WO | WO 2011/028760 A2 | 3/2011 |
| WO | WO 2011/028764 A2 | 3/2011 |
| WO | WO 2011/056546 A1 | 5/2011 |
| WO | WO 2011/116154 A2 | 9/2011 |
| WO | WO 2012/048341 A1 | 4/2012 |
| WO | WO 2012/156744 A2 | 11/2012 |
| WO | WO 2012/162296 A2 | 11/2012 |
| WO | WO 2013/006661 A2 | 1/2013 |
| WO | WO 2013/032709 A2 | 3/2013 |
| WO | WO 2013/083760 A2 | 6/2013 |
| WO | WO 2013/177220 A1 | 11/2013 |
| WO | WO 2015/069634 A1 | 5/2015 |
| WO | WO 2015/160919 A1 | 10/2015 |
| WO | WO 2016/085739 | 6/2016 |
| WO | WO 2017/066231 | 4/2017 |

OTHER PUBLICATIONS

International Search Report and Written Opinion of the International Searching Authority for International Application No. PCT/US2008/003185, dated Jan. 12, 2009.

International Preliminary Report on Patentability for PCT/US2008/003185 dated Sep. 17, 2009.

International Search Report and Written Opinion of the International Searching Authority for International Application No. PCT/US2008/008563, dated Oct. 29, 2008.

Chinese Office Action dated Jun. 18, 2012 for CN Application No. 200880127116.4.

Chinese Office Action dated May 23, 2013 for Application No. CN 200880127116.4.

Chinese Office Action dated Dec. 24, 2013 for CN Application No. 200880127116.4.

Office Communication dated Dec. 15, 2010 for Application No. EP 08865992.5.

Office Communication dated Jan. 23, 2012 for Application No. EP 08865992.5.

Office Communication dated Apr. 5, 2013 for Application No. EP 08865992.5.

Office Communication dated Aug. 29, 2013 for Application No. EP 08865992.5.

Office Communication dated Apr. 29, 2014 for EP Application No. EP 08865992.5.

Japanese Office Action dated Jul. 17, 2013 for Application No. JP 2010-539498.

Japanese Office Action dated Sep. 2, 2014 for Application No. JP 2010-539498.

International Search Report and Written Opinion of the International Searching Authority for International Application No. PCT/US2008/013912, dated Apr. 3, 2009.

International Preliminary Report on Patentability for PCT/US2008/013912 dated Jul. 1, 2010.

Invitation to Pay Additional Fees for PCT Application PCT/US09/005184 dated May 27, 2010.

International Search Report and Written Opinion from PCT Application PCT/US09/005184 dated Aug. 16, 2010.

International Preliminary Report on Patentability for PCT Application PCT/US09/005184 dated Mar. 31, 2011.

International Search Report and Written Opinion of the International Searching Authority for International Application No. PCT/US2009/003389, dated Oct. 21, 2009.

(56) References Cited

OTHER PUBLICATIONS

International Search Report and Written Opinion of the International Searching Authority for International Application No. PCT/US2009/004037, dated Oct. 2, 2009.
European Office action dated Nov. 7, 2014 for Application No. EP 09804166.8.
International Search Report and Written Opinion for International Application No. PCT/US2009/006649 dated Mar. 10, 2010.
International Preliminary Report on Patentability for International Application No. PCT/US2009/006649 dated Jun. 30, 2011.
Australian Office Action dated Dec. 17, 2013 for Application No. AU 2010315580.
Chinese Office Action dated Dec. 16, 2013 for Application No. CN 201080055990.9.
Chinese Office Action dated Jul. 30, 2014 for Application No. CN 201080055990.9.
Japanese Office Action dated Nov. 19, 2013 for Application No. JP 2012-536941.
Japanese Office Action dated Aug. 5, 2014 for Application No. JP 2012-536941.
International Search Report and Written Opinion from PCT Application PCT/US2010/054050 dated Jan. 31, 2011.
International Preliminary Report on Patentability from PCT Application PCT/US2010/054050 dated May 10, 2012.
Office Action dated Oct. 1, 2012 for U.S. Appl. No. 12/529,926.
Final Office Action dated May 28, 2013 for U.S. Appl. No. 12/529,926.
Interview Summary dated Feb. 12, 2014 for U.S. Appl. No. 12/529,926.
Office Action dated Aug. 6, 2014 for U.S. Appl. No. 12/529,926.
Office Action dated May 20, 2014 for U.S. Appl. No. 14/172,266.
Final Office Action dated Nov. 21, 2014 for U.S. Appl. No. 14/172,266.
Office Action dated May 20, 2014 for U.S. Appl. No. 14/172,326.
Final Office Action dated Nov. 20, 2014 for U.S. Appl. No. 14/172,326.
Office Action dated Jul. 30, 2014 for U.S. Appl. No. 12/809,120.
Advisory Action dated Jun. 25, 2015 for U.S. Appl. No. 12/809,120.
Advisory Action dated Mar. 21, 2014 for U.S. Appl. No. 13/119,470.
Office Action dated Jun. 24, 2015 for U.S. Appl. No. 13/119,470.
Office Action dated Feb. 28, 2013 for U.S. Appl. No. 13/139,326.
Final Office Action dated Aug. 6, 2013 for U.S. Appl. No. 13/139,326.
Advisory Action dated Nov. 20, 2013 for U.S. Appl. No. 13/139,326.
Notice of Allowance dated Jan. 27, 2014 for U.S. Appl. No. 13/139,326.
Office Action dated Sep. 17, 2013 for U.S. Appl. No. 13/503,588.
Advisory Action dated May 16, 2014 for U.S. Appl. No. 13/503,588.
[No Author] Microfluidic ChipShop. Microfluidic product catalogue. Mar. 2005.
[No Author] Microfluidic ChipShop. Microfluidic product catalogue. Oct. 2009.
Abate et al., Droplet Based Sequencing. American Physical Society. Presentation. Mar. 12, 2008. 25 pages.
Abate et al., Valve-based flow focusing for drog formation. Appl Phys Lett. 2009;94. 3 pages. (Month not cited on publication).
Agresti, "Selection of ribozymes that catalyse multiple-turnover Diels-Alder cycloadditions by using in vitro compartmentalization", PNAS, 102, 16170-16175 (2005). (Nov. 2005).
Akselband, "Enrichment of slow-growing marine microorganisms from mixed cultures using gel microdrop (GMD) growth assay and fluorescence-activated cell sorting", J. Exp. Marine Biol., 329: 196-205 (2006). (Month not cited on publication).
Akselband, "Rapid mycobacteria drug susceptibility testing using gel microdrop (GMD) growth assay and flow cytometry", J. Microbiol. Methods, 62:181-197 (2005). (Month not cited on publication).
Anna et al., Formation of dispersions using 'flow focusing' in microchannels. Appln Phys Letts. 2003;82(3):364-66. (Jan. 2003).
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32. (Feb. 2003).
Carroll, "The selection of high-producing cell lines using flow cytometry and cell sorting", Exp. Op. Biol. Therp., 4:11 1821-1829 (2004). (Month not cited on publication).
Chaudhary "A rapid method of cloning functional variable-region antibody genese in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101. (Month not cited on publication).
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, L., et al., "Controllable Monodisperse Multiple Emulsions," Angew. Chem. Int. Ed., vol. 46, pp. 8970-8974 (2007). (Month not cited on publication).
Clausell-Tormos et al., "Droplet-based microfluidic platforms for the encapsulation and screening of mammalian cells and multicellular organisms", Chem. Biol. 15:427-437 (2008). (May 2008).
De Bruin et al., UBS Investment Research. Q-Series®: DNA Sequencing. UBS Securities LLC. Jul. 12, 2007. 15 pages.
Diaz, R.V., et al., "One-Month sustained release microspheres of 125 I-bovine calcitonin In vitro-in vivo studies," Journal of Controlled Release, vol. 59, pp. 55-62 (1999). (Month not cited on publication).
Doerr, The smallest bioreactor. Nature Methods. 2005; 2(5):326. (May 2005).
Drmanac eta l., Sequencing by hybridization (SBH): advantages, achievements, and opportunities. Adv Biochem Eng Biotechnol. 2002;77:75-101. (Month not cited on publication).
Fu, "A microfabricated fluorescence-activated cell sorter", Nature Biotech., 17:1109-1111 (1999). (Nov. 1999).
Fulton et al., Advanced multiplexed analysis with the FlowMetrix system. Clin Chem. Sep. 1997;43(9):1749-56.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
He et al., "Selective Encapsulation of Single Cells and Subcellular Organelles into Picoliter- and Femtoliter-Volume Droplets" Anal. Chem 77: 1539-1544 (2005) (Mar. 2005).
Holtze et al., Biocompatible surfactants for water-in-fluorocarbon emulsions. Lab Chip. Oct. 2008; 8(10):1632-9.
Huebner, "Quantitative detection of protein expression in single cells using droplet microfluidics", Chem. Commun. 1218-1220 (2007). (Month not cited on publication).
Hug et al. Measurement of the number of molecules of a single mRNA species in a complex mRNA preparation. J Theor Biol. Apr. 21, 2003; 221(4):615-24.
Khomiakova et al., [Analysis of perfect and mismatched DNA duplexes by a generic hexanucleotide microchip]. Mol Biol (Mosk). Jul.-Aug. 2003;37(4):726-41. Russian.
Kim et al., Fabrication of monodisperse gel shells and functional micro gels in microfluidic devices. Angew Chem Int Ed Engl. Mar. 2007;46(11):1819-22.
Kim, "Fabrication of monodisperse gel shells and functional microgels in microfluidic devices", Angew. Chem., 119:1851-1854 (2007).
Kim, J., et al, "Albumin loaded microsphere of amphiphilic poly-(ethylene glycol)/poly(a-ester) multiblock copolymer," European Journal of Pharmaceutical Sciences, vol. 23, pp. 245-251 (2004). (Month not cited on publication).
Koster et al., "Drop-based microfluidic devices for encapsulation of single cells", Lab on a Chip The Royal Soc. of Chem. 8:1110-1115 (2008). (Month not cited on publication).
Li, Y., et al., "PEGylated PLGA nanoparticles as protein carriers: synthesis, preparation and biodistribution in rats," Journal of Controlled Release, vol. 71, pp. 203-211 (2001). (Month not cited on publication).

(56) References Cited

OTHER PUBLICATIONS

Loscertales, Micro/Nano encapsulation via electrified coaxial liquid jets. Science. 2002;295:1695-98. (Mar. 2002).
Love, A microengraving method for rapid selection of single cells producing antigen-specific antibodies. Nature Biotech. Jun. 2006:24(6):703-07.
Mazutis et al., Selective droplet coalescence using microfluidic systems. Lab Chip. Apr. 24, 2012; 12(10):1800-6.
Mirzabekov, "DNA Sequencing by Hybridization—a Megasequencing Method and A Diagnostic Tool?" Trends in Biotechnology 12(1): 27-32 (1994) (Jan. 1994).
Mouritzen et al., Single nucleotide polymorphism genotyping using locked nucleic acid (LNA). Expert Rev Mol Diagn. Jan. 2003;3(1):27-38.
Nguyen, "In situ hybridization to chromosomes stabilized in gel microdrops", Cytometry, 21:111-119 (1995). (Month not cited on publication).
Okushima, "Controlled production of monodisperse double emulsions by two-step droplet breakup in microfluidic devices", Langmuir, 20:9905-9908 (2004). (Month not cited on publication).
Perez, C., et al., "Poly(lactic acid)-poly(ethylene glycol) nanoparticles as new carriers for the delivery of plasmid DNA," Journal of Controlled Release, vol. 75, pp. 211-224 (2001). (Month not cited on publication).
Ryan, "Rapid assay for mycobacterial growth and antibiotic susceptibility using gel microdrop and encapsulation", J. Clinical Microbiol., 33:7 1720-1726 (1995). (Jul. 1995).
Schirinzi et al., Combinatorial sequencing-by-hybridization: analysis of the NF1 gene. Genet Test. 2006 Spring;10(1):8-17. (Month not cited on publication).
Schmitt, "Bead-based multiplex genotyping of human papillomaviruses", J. Clinical Microbiol., 44:2 504-512 (2006). (Feb. 2006).
Shah, "Fabrication of monodisperse thermosensitive microgels and gel capsules in microfluidic devices", Soft Matter, 4:2303-2309 (2008). (Month not cited on publication).
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, et al. Man-made cell-like compartments for molecular evolution. Nat Biotechnol. Jul. 1998;16(7):652-6.
Van De Hulst et al., Glare points. Appl Opt. Nov. 20, 1991;30(33):4755-63.
Wang et al., Single nucleotide polymorphism discrimination assisted by improved base stacking hybridization using oligonucleotide microarrays. Biotechniques. 2003;35:300-08. (Aug. 2003).
Weaver, "Rapid clonal growth measurements at the single-cell level: gel microdroplets and flow cytometry", Biotechnology, 9:873-877 (1991). (Sep. 1991).
Whitesides, "Soft lithography in biology and biochemistry", Annual Review of Biomedical Engineering, 3:335-373 (2001). (Month not cited on publication).
Xia, "Soft lithography", Annual Review of Material Science, 28:153-184 (1998). (Month not cited on publication).
Zhang, "Combinatorial marking of cells and organelles with reconstituted fluorescent proteins", Cell, 119:137-144 (Oct. 1, 2004).
Zhao, J., et al., "Preparation of hemoglobin-loaded nano-sized particles with porous structure as oxygen carriers," Biomaterials, vol. 28, pp. 1414-1422 (2007). Available online Nov. 2006.
Zimmerman, Microscale production of hybridomas by hypoosmolar electrofusion. Hum Antibod Hybridomas. Jan. 3, 1992:14-18.
European Office Action for Application No. EP 09758762.0 dated Aug. 13, 2015.
European Office Action for Application No. 09758762.0 dated Sep. 29, 2016.
Korean Office Action for Application No. KR 10-2011-7000094 dated Feb. 27, 2013.
International Search Report and Written Opinion for International Application No. PCT/US09/003389 dated Oct. 21, 2009.
International Preliminary Report on Patentability for International Application No. PCT/US2009/003389 dated Dec. 16, 2010.
International Search Report and Written Opinion dated Jan. 10, 2017 for Application No. PCT/US2016/056509.
Final Office Action for U.S. Appl. No. 13/119,470 dated Dec. 5, 2013.
Office Action for U.S. Appl. No. 12/993,205 dated Jul. 11, 2012.
Office Action for U.S. Appl. No. 12/993,205 dated Feb. 14, 2013.
Office Action dated Feb. 24, 2015 for U.S. Appl. No. 13/397,018.
Office Action for U.S. Appl. No. 13/967,018 dated Jun. 11, 2015.
Office Action for U.S. Appl. No. 13/967,018 dated Feb. 9, 2016.
Office Action for U.S. Appl. No. 13/967,018 dated Jun. 30, 2016.
Office Action for U.S. Appl. No. 13/967,018 dated Dec. 23, 2016.
[No Author Listed], Toxnet, Toxicology Data Network. Vinyl Toluene. National Library of Medicine. 2015:1-38.
[No Author] Gene Characterization Kits. Stratagene Catalog. Statagene Cloning Systems: Tools and Technology for Lift Sciences. 1988. 3 pages.
Adams et al., Entropically driven microphase transitions in mixtures of colloidal rods and spheres. Nature. May 28, 1998:393:349-52.
Dendukuri et al. Continuous-flow lithography for high-throughput microparticle synthesis. Nature Mat. May 2006;5:365-69.
Durant et al., Effects of cross-linking on the morphology of structured latex particles 1. Theoretical considerations. Macromol. 1996;29:8466-72. Month not cited on publication.
Gordon et al., Self-assembled polymer membrane capsules inflated by osmotic pressure. JACS. 2004;126:14117-22. Published on web Oct. 12, 2004.
Graham et al., Nanogels and microgels: The new polymeric materials playground. Pure Appl Chem. 1998;70(6):1271-75. Month not cited on publication.
Hsu et al., Self-assembled shells composed of colloidal particles: fabrication and characterization. Langmuir. 2005;21:2963-70. Published on web Feb. 23, 2005.
Jogun et al., Rheology and microstructure of dense suspensions of plate-shaped colloidal particles. J. Rheol. Jul./Aug. 1999;43:847-71.
Kim et al., Colloidal assembly route for responsive colloidsomes with tunable permeability. Nano Lett. 2007;7:2876-80. Published on web Aug. 3, 2007.
Kim et al., Fabrication of monodisperse gel shells and functional microgels in microfluidic devices. Angew Chem Int Ed. 2007;46:1819-22. Month not cited on publication.
Kim et al., Monodisperse nonspherical colloid materials with well-defined structures. Presentation. Sep. 16, 2005. 5 pages.
Kim et al., Synthesis of nonspherical colloidal particles with anisotropic properties. JACS. 2006;128:14374-77. Published on web Oct. 18, 2006.
Kim et al., Uniform nonspherical colloidal particles engineered by geometrically tunable gradient of crosslink density. $80^{th}$ ACS Colloid Surf. Sci. Symp. Jun. 20, 2006. 23 pages.
Kim et al., Uniform nonspherical colloidal particles with tunable shapes. Adv. Mater. 2007;19:2005-09. Month not cited on publication.
Koo et al., A snowman-like array of colloidal dimers for antireflecting surfaces. Adv Mater. Feb. 3, 2004;16(3):274-77.
Kumar et al., Biodegradable block copolymers. Adv Drug Deliv Rev. Dec. 3, 2001;53(1):23-44.

(56) References Cited

OTHER PUBLICATIONS

Landfester et al. Preparation of Polymer Particles in Nonaqueous Direct and Inverse Miniemulsions. Macromolecules. Mar. 11, 2000;33(7):2370-2376.
Landfester et al., Formulation and Stability Mechanisms of Polymerizable Miniemulsions. Macromolecules. 1999;32:5222-5228. Published on web Jul. 22, 1999.
Lee et al., Double emulsion-templated nanoparticle colloidosomes with selective permeability. Adv Mater. 2008;20:3498-503. Month not cited on publication.
Lin et al., Ultrathin cross-linked nanoparticle membranes. JACS. 2003;125:12690-91. Published on web Sep. 27, 2003.
Lorenceau et al., Generation of polymerosomes from double-emulsions. Langmuir. Sep. 27, 2005;21(20):9183-6.
Manoharan et al., Dense packing and symmetry in small clusters of microspheres. Science. Jul. 25, 2003;301:483-87.
Mock et al., Synthesis of anisotropic nanoparticles by seeded emulsion polymerization. Langmuir. Apr. 25, 2006;22(9):4037-43. Published on web Mar. 31, 2006.
Nikolaides et al., Two Dimensional Crystallisation on Curved Surfaces. MRS Fall 2000 Meeting. Boston, MA. Nov. 27, 2000. Abstract #41061.
Okubo et al., Micron-sized, monodisperse, snowman/confetti-shaped polymer particles by seeded dispersion polymerization. Colloid Polym. Sci. 2005;283:1041-45. Published online Apr. 2, 2005.
Reculusa et al., Synthesis of daisy-shaped and multipod-like silica/polystyrene nanocomposites. Nano Lett. 2004;4:1677-82. Published on web Jul. 14, 2004.
Roh et al., Biphasic janus particles with nanoscale anisotropy. Nature Med. Oct. 2005;4:759-63.
Sheu et al., Phase separation in polystyrene latex interpenetrating polymer networks. J. Poly. Sci. A. Poly. Chem. 1990;28:629-51. Month not cited on publication.
Shum et al., Double emulsion templated monodisperse phospholipid vesicles. Langmuir. Aug. 5, 2008;24(15):7651-3. Epub Jul. 10, 2008.
Shum et al., Microfluidic fabrication of monodisperse biocompatible and biodegradable polymersomes with controlled permeability. J Am Chem Soc. Jul. 23, 2008;130(29):9543-9. Epub Jun. 25, 2008.
Skjeltorp et al., Preparation of nonspherical, monodisperse polymer particles and their self-organization. J. Colloid Interf. Sci. Oct. 1986;113:577-82.
Ulrich, Chapter 1. General Introduction. Chem. Tech. Carbodiimides. 2007:1-7. Month not cited on publication.
Van Blaaderen, Colloidal molecules and beyond. Science. Jul. 25, 2003;301:470-71.
Van Blaaderen, Colloids get complex. Nature. Feb. 2006;439:545-46.
Velev et al., Assembly of latex particles by using emulsion droplets. 3. Reverse (water in oil) system. Langmuir. 1997;13:1856-59. Month not cited on publication.
Velev et al., Assembly of latex particles using emulsion droplets as templates. 1. Microstructured hollow spheres. Langmuir. 1996;12:2374-84. Month not cited on publication.
Velev et al., Assembly of latex particles using emulsion droplets as templates. 2. Ball-like and composite aggregates. Langmuir. 1996;12:2385-91. Month not cited on publication.
Weitz, Nonspherical engineering of polymer colloids. Web Page. Exp. Soft Condensed Matter Group. Last updated Nov. 10, 2005. 1 page.
Weitz, Packing in the spheres. Science. Feb. 13, 2004;303:968-969.
Yin et al., Template-assisted self-assembly: a practical route to complex aggregates of monodispersed colloids with well-defined sizes, shapes, and structures. JACS. 2001;123:8718-29. Published on web Aug. 15, 2001.
Extended European Search Report for Application No. EP 14860623.9 dated May 23, 2017.
International Search Report and Written Opinion from PCT Application PCT/US2014/063846 dated Mar. 10, 2015.
Invitation to Pay Additional Fees from PCT Application PCT/US2014/063846 dated Jul. 1, 2015.
International Preliminary Report on Patentability from PCT Application PCT/US2014/063846 dated May 19, 2016.
Office Action for U.S. Appl. No. 13/119,470 dated Apr. 24, 2013.
Office Action for U.S. Appl. No. 13/119,470 dated Feb. 1, 2018.
Office Action for U.S. Appl. No. 14/812,930 dated Nov. 13, 2017.
Office Action for U.S. Appl. No. 14/812,942 dated Feb. 1, 2018.
Office Action for U.S. Appl. No. 14/812,946 dated Jan. 25, 2018.
Office Communication for U.S. Appl. No. 14/812,954 dated Dec. 7, 2017.
Office Action for U.S. Appl. No. 14/812,964 dated Jan. 25, 2018.
Office Action for U.S. Appl. No. 15/035,167 dated Nov. 27, 2017.
Office Action for U.S. Appl. No. 15/035,167 dated Apr. 2, 2018.
Baret et al., Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Draget et al., Alginate based new materials. Int J Biol Macromol. Aug. 1997;21(1-2):47-55.
Khatiwala et al., "Intrinsic mechanical properties of the extracellular matrix affect the behaviour of pre-osteoblastic MC3T3-E1 cells" Am. J. Physiol. Cell Physiol. 2006;290:C1640.
Khetani et al., Microscale culture of human liver cells for drug development. Nat Biotechnol. Jan. 2008;26(1):120-6. Epub Nov. 18, 2007.
Klein et al., Cell-cycle control by physiological matrix elasticity and in vivo tissue stiffening. Curr Biol. Sep. 29, 2009;19(18):1511-8. doi: 10.1016/j.cub.2009.07.069. Epub Sep. 17, 2009.
Kumaresan et al. High-Throughput Single Copy DNA Amplification and Cell Analysis in Engineered Nanoliter Droplets. Anal Chem. 2008. 80:3522-3529.
Park et al., Shear-reversibly crosslinked alginate hydrogels for tissue engineering. Macromol Biosci. Sep. 9, 2009;9(9):895-901. doi: 10.1002/mabi.200800376.
Rimann et al., Synthetic 3D multicellular systems for drug development. Curr Opin Biotechnol. Oct. 2012;23(5):803-9. doi:10.1016/j.copbio.2012.01.011. Epub Feb. 10, 2012.
Sakai et al., Both ionically and enzymatically crosslinkable alginate-tyramine conjugate as materials for cell encapsulation. J Biomed Mater Res A. May 2008;85(2):345-51.
Schmitz et al., Dropspots: a picoliter array in a microfluidic device. Lab Chip. Jan. 7, 2009;9(1):44-9. doi: 10.1039/b809670h. Epub Oct. 28, 2008.
Schürch et al., "Potential of plant cells in culture for cosmetic applications." Phytochem. Rev. 2008;7:599.
Shintaku et al. (Microsystem technologies 13.8-10 (2007): 951-958; published online Dec. 1, 2006 (Year: 2006).
Tan et al., "Monodisperse Alginate Hydrogel Microbeads for Cell Encapsulation" Adv. Mater. 2007;19:2696.
Zhang et al., "Exploring Microfluidic Routes to Microgels of Biological Polymers." Macromol. Rapid. Commun. Volume 280, Issue 5, p. 327 (2007).
Zhang et al., "Microfluidic Production of Biopolymer Microcapsules with Controlled Morphology." JACS. 2006;128:12205.
Office Action for U.S. Appl. No. 13/119,470 dated Nov. 20, 2018.
Office Action for U.S. Appl. No. 14/812,930 dated Jun. 22, 2018.
Office Action for U.S. Appl. No. 14/812,930 dated Nov. 20, 2018.
Office Action for U.S. Appl. No. 14/812,942 dated Jul. 13, 2018.
Office Action for U.S. Appl. No. 14/812,946 dated Jul. 27, 2018.
Office Action for U.S. Appl. No. 14/812,954 dated Jun. 22, 2018.
Office Action for U.S. Appl. No. 14/812,954 dated Nov. 19, 2018.
Office Action for U.S. Appl. No. 14/812,964 dated Nov. 19, 2018.
U.S. Appl. No. 15/670,977, filed Aug. 7, 2017, Weitz et al.
U.S. Appl. No. 15/792,218, filed Oct. 24, 2017, Weitz et al.
U.S. Appl. No. 15/915,686, filed Mar. 8, 2018, Weitz et al.
EP 16856059.7, Apr. 1, 2019, Extended European Search Report.
PCT/US2016/056509, Apr. 26, 2018, International Preliminary Report on Patentability.
PCT/US2018/047053, Oct. 23, 2018, International Search Report and Written Opinion.
Office Action for U.S. Appl. No. 13/119,470 dated Jun. 25, 2019.
Office Action for U.S. Appl. No. 14/812,930 dated Jun. 25, 2019.
Office Action for U.S. Appl. No. 14/812,942 dated Jan. 28, 2019.

(56) References Cited

OTHER PUBLICATIONS

Office Action for U.S. Appl. No. 14/812,946 dated Feb. 7, 2019.
Office Action for U.S. Appl. No. 14/812,954 dated Jun. 21, 2019.
Office Action for U.S. Appl. No. 14/812,964 dated Jun. 21, 2019.
Office Action for U.S. Appl. No. 15/768,135 dated Dec. 27, 2018.
Office Action for U.S. Appl. No. 15/768,135 dated May 29, 2019.
Office Action for U.S. Appl. No. 15/915,686 dated Mar. 12, 2019.
Extended European Search Report for Application No. EP 16856059.7 dated Apr. 1, 2019.
International Preliminary Report on Patentability from Application No. PCT/US2016/056509 dated Apr. 26, 2018.
International Search Report and Written Opinion for Application No. PCT/US2018/047053 dated Oct. 23, 2018.
Office Action for U.S. Appl. No. 13/119,470 dated Oct. 4, 2019.
Office Action for U.S. Appl. No. 14/812,930 dated Oct. 4, 2019.
Office Action for U.S. Appl. No. 14/812,942 dated Sep. 12, 2019.
Office Action for U.S. Appl. No. 14/812,946 dated Sep. 12, 2019.
Office Action for U.S. Appl. No. 14/812,954 dated Oct. 7, 2019.
Office Action for U.S. Appl. No. 14/812,964 dated Oct. 7, 2019.
Office Action for U.S. Appl. No. 15/768,135 dated Oct. 25, 2019.
Chinese Office Action dated May 8, 2020 for Application No. CN 201680068910.0.
International Preliminary Report on Patentability for Application No. PCT/US2018/047053 dated Mar. 5, 2020.
European Office Action for Application No. EP 14860623.9 dated Nov. 12, 2019.
Office Action for U.S. Appl. No. 13/119,470 dated Apr. 8, 2020.
Office Action for U.S. Appl. No. 14/812,930 dated Apr. 8, 2020.
Office Action for U.S. Appl. No. 14/812,942 dated Mar. 18, 2020.
Office Action for U.S. Appl. No. 14/812,946 dated Mar. 18, 2020.
Office Action for U.S. Appl. No. 14/812,954 dated Apr. 8, 2020.
Office Action for U.S. Appl. No. 14/812,964 dated Apr. 9, 2020.
Office Action for U.S. Appl. No. 15/768,135 dated Feb. 18, 2020.
Office Action for U.S. Appl. No. 16/576,230 dated May 8, 2020.
U.S. Appl. No. 16/431,354, filed Jun. 4, 2019, Weitz et al.
U.S. Appl. No. 16/779,501, filed Jan. 31, 2020, Weitz et al.
U.S. Appl. No. 13/119,470, filed May 4, 2011, Weitz et al.
U.S. Appl. No. 14/812,930, filed Jul. 29, 2015, Weitz et al.
U.S. Appl. No. 14/812,942, filed Jul. 29, 2015, Weitz et al.
U.S. Appl. No. 14/812,946, filed Jul. 29, 2015, Weitz et al.
U.S. Appl. No. 14/812,954, filed Jul. 29, 2015, Weitz et al.
U.S. Appl. No. 14/812,964, filed Jul. 29, 2015, Weitz et al.
U.S. Appl. No. 16/576,230, filed Sep. 19, 2019, Weitz et al.
CN 201680068910.0, May 8, 2020, Chinese Office Action.
PCT/US2018/047053, Mar. 5, 2020, International Preliminary Report on Patentability.
EP 14860623.9, Nov. 12, 2019, European Office Action.
Office Action for U.S. Appl. No. 15/768,135 dated Jun. 19, 2020.
U.S. Appl. No. 15/768,135, filed Apr. 13, 2018, Weitz et al.
JP 2018519002, Oct. 28, 2020, Japanese Office Action.
CN 201680068910.0, Mar. 8, 2021, Chinese Office Action.
Japanese Office Action dated Oct. 28, 2020 for Application No. JP 2018-519002.
Chinese Office Action dated Mar. 8, 2021 for Application No. CN 201680068910.0.
Office Action for U.S. Appl. No. 15/768,135 dated Feb. 17, 2021.
U.S. Appl. No. 17/148,796, filed Jan. 14, 2021, Weitz et al.
U.S. Appl. No. 16/640,598, filed Feb. 20, 2020, Weitz et al.
AU 2016338907, Jun. 5, 2021, Australian Exam Report.
CN 201680068910.0, Aug. 4, 2021, Chinese Office Action.
JP 2018-519002, May 13, 2021, Japanese Office Action.
Australian Exam Report for Application No. AU 2016338907 dated Jun. 5, 2021.
Chinese Office Action for Application No. CN 201680068910.0 dated Aug. 4, 2021.
Japanese Office Action for Application No. JP 2018-519002 dated May 13, 2021.
Fernandes et al., Solubility of Irgacure® 2959 Photoinhibitor In Supercritical Carbon Dioxide: Experimental Determination and Correlation. AIChe Annual Meeting, Nov. 7, 2007, No. 449d: p. 1-3.

\* cited by examiner

X = NUCLEIC ACID
RESIDUE
XXXX

Fig. 7A

XXXXX

Fig. 7B

XXXXXX

L = LOCKED
NUCLEIC ACID
XXLXX—(S)

Fig. 7F

CREATION OF LIBRARIES OF DROPLETS AND RELATED SPECIES

RELATED APPLICATIONS

This application is a continuation of Ser. No. 13/119,470, with a filing date of May 4, 2011 which is a national stage filing under 35 U.S.C. § 371 of International Application Serial No. PCT/US2009/005184, filed Sep. 17, 2009, which claims the benefit of U.S. Provisional Patent Application Ser. No. 61/098,674, filed Sep. 19, 2008, entitled "Creation of Libraries of Droplets and Related Species," by Weitz, et al., herein incorporated by reference.

GOVERNMENT FUNDING

This invention was made with government support under DMR-0602684 awarded by the National Science Foundation. The government has certain rights in the invention.

FIELD OF INVENTION

The present invention is generally related to systems and methods for producing a plurality of droplets. The droplets may contain varying species, e.g., for use as a library. The droplets may be rigidified and/or fluidized, in some cases.

BACKGROUND

Various technologies have been developed that allow production of "libraries" of synthetic compounds (e.g., pharmaceutical agents, inhibitors, etc.) or nucleic acid probes, etc. A library of synthetic compounds may be used to screen for a target analyte molecule (e.g., an enzymes, an antibody, etc.) having a desired activity. Although current libraries are valuable, commercially-available resources useful in the search to identify new compounds with desirable activities, there are practical difficulties (e.g., cost, time, equipment, etc.) associated with the preparation, storage, and use of current technologies.

SUMMARY OF THE INVENTION

The present invention is generally related to systems and methods for producing a plurality of droplets. The droplets may be rigidified and/or fluidized, in some cases. The subject matter of the present invention involves, in some cases, interrelated products, alternative solutions to a particular problem, and/or a plurality of different uses of one or more systems and/or articles.

In one aspect, the invention is directed to a method. According to a first set of embodiments, the method includes acts of providing a plurality of droplets, each of the plurality of droplets comprising a first fluid and being surrounded by a second fluid, wherein the first fluid and the second fluid are substantially immiscible, causing at least some of the plurality of droplets to undergo a phase change to form a plurality of rigidified droplets, exposing the plurality of rigidified droplets to a third fluid, wherein the third fluid is substantially miscible in the first fluid, and adding at least one first species internally to at least some of the rigidified droplets.

In one set of embodiments, the method includes acts of providing a plurality of groups of rigidified droplets, each of the groups of rigidified droplets comprising a first fluid and having substantially the same composition as the other groups of rigidified droplets but containing a distinguishable species with respect to the other groups of rigidified droplets, forming a suspension comprising at least one rigidified droplet from each of the groups of rigidified droplets, exposing at least some of the rigidified droplets of the suspension to a second fluid, wherein the first fluid and the second fluid are substantially immiscible, and fluidizing at least some of the rigidified droplets to form a plurality of fluidized droplets, wherein the plurality of fluidized droplets are substantially immiscible in the second fluid.

In another set of embodiments, the method includes acts of providing a first plurality of rigidified droplets, each rigidified droplet being surrounded by a second fluid, the rigidified droplets being formed from a fluidic droplet comprising a first fluid, wherein the second fluid is substantially immiscible in the first fluid, exposing the first plurality of rigidified droplets to a third fluid, wherein the third fluid is substantially miscible in the first fluid, adding at least one first species internally to at least some of the first plurality of rigidified droplets to form a first group of species-containing droplets, repeating the above acts with a second plurality of rigidified droplets and a second species to form a second group of species-containing droplets, and forming a suspension comprising at least some droplets of the first and second groups of species-containing droplets.

In still another set of embodiments, the method includes the acts of providing a plurality of droplets, each of the plurality of droplets comprising a first fluid and being surrounded by a second fluid, wherein the first fluid and the second fluid are substantially immiscible, causing at least some of the plurality of microfluidic droplets to undergo a phase change to form a plurality of rigidified droplets, exposing the plurality of rigidified droplets to a third fluid, wherein the third fluid is substantially miscible in the first fluid, separating the plurality of rigidified fluidic droplets into at least a first group of rigidified droplets and a second group of rigidified droplets, adding at least one first species internally to at least some of the rigidified droplets of the first group and at least one second species internally to at least some of the rigidified droplets from the second group, wherein the second species is distinguishable from the first species, forming a suspension comprising at least one rigidified droplet from each of the groups of rigidified droplets, fluidizing at least some of the rigidified droplets to form a plurality of fluidized droplets, and forming a plurality of microfluidic droplets, wherein each microfluidic droplet comprises at least one rigidified droplet.

In still yet another set of embodiments, the method includes the acts of providing a first plurality of rigidified droplets, immobilizing at least one first species internally with respect to at least some of the first plurality of rigidified droplets to form a first group of species-containing droplets, repeating the above acts with a second plurality of rigidified droplets and a second species to form a second group of species-containing droplets, and forming a suspension comprising at least some droplets of the first and second groups of species-containing droplets.

In another aspect, the invention is directed to a composition. In some cases, the composition comprises a container comprising at least eight mutually distinguishable rigidified droplets, each having substantially the same composition but containing a distinguishable species with respect to the other rigidified droplets.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 7A-7F show non-limiting examples of nucleic acid probes.

DETAILED DESCRIPTION

Figure 1:
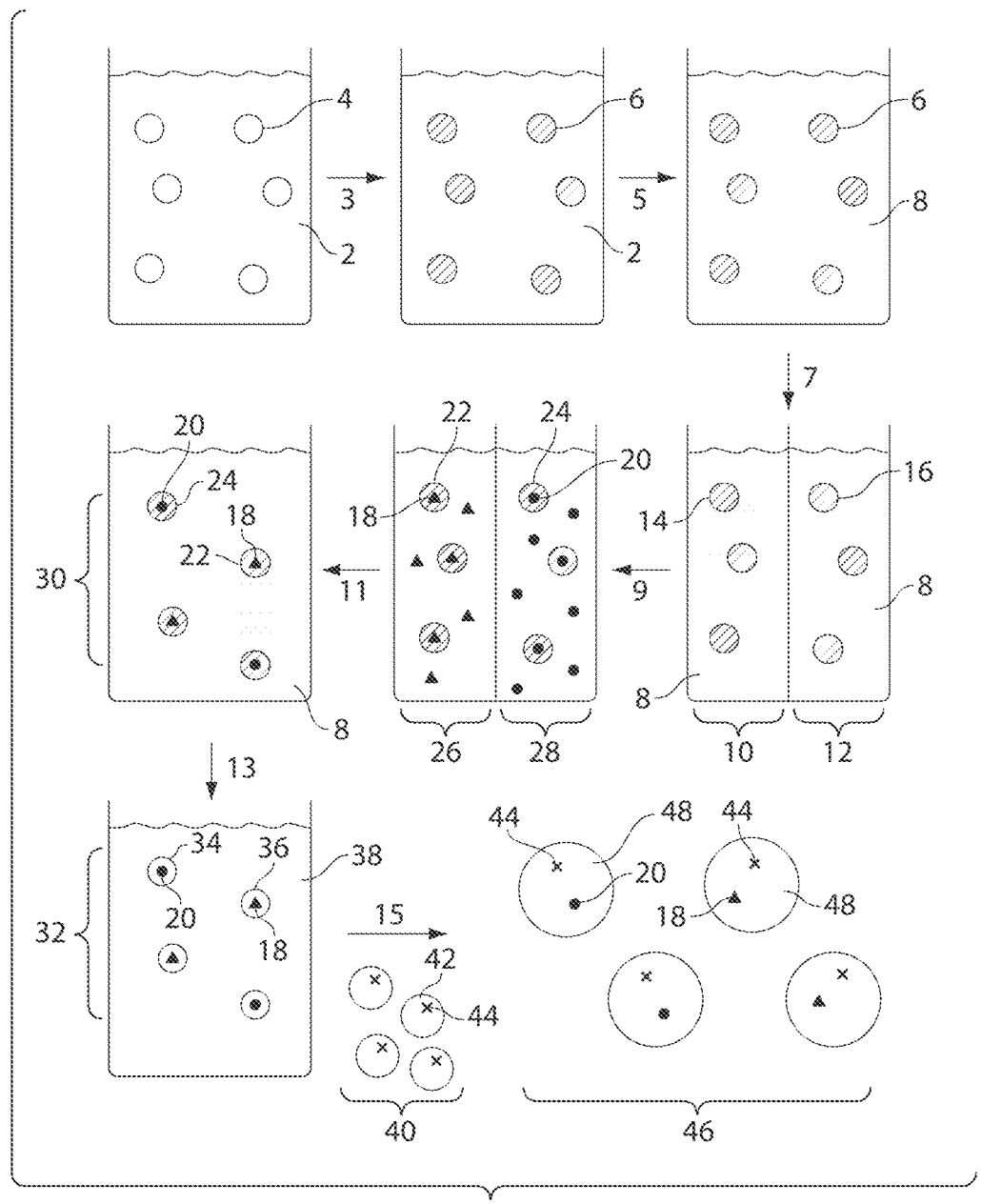
FIG. 1 depicts a method for forming a suspension comprising two groups of droplets and for fusing the suspension of droplets with a plurality of analyte droplets, according to some embodiments of the present invention.

The present invention is generally related to systems and methods for producing a plurality of droplets. The droplets may contain varying species, e.g., for use as a library. In some cases, the fluidic droplets may be rigidified to form rigidified droplets (e.g., gel droplets). The droplets may undergo a phase change (e.g., from rigidified droplets to fluidized droplets), as discussed more herein. In some cases, a species may be added internally to a droplet, such as a rigidified droplet by exposing the droplet to a fluid comprising the species. After introduction, the species may be contained within the droplet, for instance, reacted within the droplet, and/or the fluid surrounding the droplet may be replaced by a fluid that is relatively unfavorable to the species.

The present invention, in some embodiments, provides methods for forming a composition comprising a plurality of droplets, where the droplets may be fluidic or rigid. In some cases, the method provides a plurality of droplets containing a first fluid and being substantially surrounded by a second fluid, where the first fluid and the second fluid are substantially immiscible (e.g., droplets containing an aqueous-based liquid being substantially surrounded by an oil-based liquid). At least some of the droplets may be caused to undergo a phase change to form a plurality of rigidified droplets (e.g., a plurality of gel droplets). The gel droplets may be exposed to a third fluid which is substantially miscible with the first fluid (e.g., an aqueous-based liquid) and the rigidified droplets may be separated into at least a first group of rigidified droplets and a second group of rigidified droplets. At least one first species may be added internally to some of the first group of rigidified droplets and at least one second species may be added internally to the second group of rigidified droplets, where the first species and the second species are distinguishable with respect to the other species. A suspension may be formed comprising at least one of the first group of species-containing droplet and at least one of the second group of species-containing droplets. In some cases, the suspension of rigidified species-containing droplets may be fluidized (e.g., phase change from a gel to a liquid) and a plurality of fluidized droplets may be formed. In certain embodiments, a plurality of microfluidic droplets is formed (e.g., by fusing the rigidified droplet with another fluidic droplet) which each comprise at least one fluidized droplet, and in some cases, as least one target analyte molecule.

In some embodiments, the invention provides systems and methods for forming a plurality of droplets, where the plurality of droplets comprises various groups of droplets containing at least one distinguishable species with respect to other groups. For example, the plurality of droplets may comprise a first group of droplets and a second group of droplets, where each of the first group of droplets contains a first species and each of the second group of droplets contains a second species. The plurality of droplets can be formed by providing a plurality of rigidified droplets (e.g., gel droplets) containing a first fluid, substantially surrounded by a second fluid. The plurality of rigidified droplets may be exposed to a third fluid (which may be substantially miscible with the first fluid), and at least one species may be added internally to each droplet.

The addition of a species to a droplet may be accomplished using any suitable technique. In one embodiment, the species is added to the droplet by allowing the species to diffuse from the fluid substantially surrounding the droplet into fluid contained within the droplet. This may be repeated for a second group of rigidified droplets and a second species. In some cases, at least some of the first group of rigidified droplets and the second group of rigidified droplets may be combined within a common suspension comprising the first and second droplets.

A non-limiting example of one embodiment of the invention is depicted is FIG. 1. In this figure, a plurality of droplets 4 comprising a first fluid are substantially surrounded by second fluid 2. In some cases, the first fluid and the second fluid may be substantially immiscible such that the plurality of droplets 4 do not coalesce or dissolve with second fluid 2. However, in other cases, as discussed below, the first fluid and the second fluid need not be substantially immiscible. The plurality of droplets 2, in FIG. 1, is caused to undergo a phase change to form a plurality of rigidified droplets 6, as indicated by arrow 3. The phase change may be induced, for example, by altering the temperature of the droplets, by a chemical reaction, or the like. For instance, the droplets may comprise a material such as agarose, which forms a gel when the polymer is cooled to a temperature below its gelling temperature.

In FIG. 1, the plurality of rigidified droplets 6 is then exposed to a third fluid 8, as indicated by arrow 5. Third fluid 8 may be substantially immiscible with second fluid 2 and/or substantially miscible with the first fluid, although in some cases, as discussed below, these are not requirements. In some cases, for instance, if the plurality of droplets 4 were exposed to third fluid 8 before the phase change described above, droplets 4 may coalesce with third fluid 8, for instance if droplets 4 were aqueous-based, second fluid 2 was oil-based, and third fluid 8 was also aqueous-based. Accordingly, by rigidifying droplets 4, coalescence with third fluid 8 may be avoided or at least reduced in some embodiments.

In some cases, the rigidified droplets are exposed to a variety of conditions. For instance, the rigidified droplets may be exposed to various species, environmental conditions, or the like. In this example, the rigidified droplets have substantially the same composition, which may be useful in reducing differences due to the production of the droplets themselves, as opposed to the varying conditions the droplets were subsequently exposed to. For instance, referring again to FIG. 1, the plurality of rigidified droplets may be separated into a first group 10 of rigidified droplets 14 and a second group 12 of rigidified droplet 16, as indicated by arrow 7. As shown in FIG. 1, the first group and second group are divided by a partition within the same vessel; however, in other cases, the groups may be contained within separate vessels, or the groups may be separate aliquots or samples, etc. The droplets may also be separated into more than two groups in other embodiments, as discussed below; only two groups are presented in FIG. 1 for reasons of clarity. In this figure, at least one first species 18 is introduced into at least some of first group 10 of rigidified droplets 14 to form a first group 26 of species-containing droplets 22, as follows. First species 18 may be present in third fluid 8 (for example, added to third fluid 8 after separation of first group 10), and is allowed to associate with or be contained internally in the droplet, e.g., via diffusion, chemical reaction, etc. Next, the suspension of droplets may be exposed to a fourth fluid 38. The fourth fluid may or may not be the same fluid as the second fluid, and in some cases, the fourth fluid may be substantially immiscible with the first fluid. In some cases, fourth fluid 32 is chosen such that species 22 is not able to substantially leave droplets 14 to enter fourth fluid 32 (e.g., due to differences in solubility). However, in other cases, e.g., when species 22 is chemically reacted with droplet 14, the fourth fluid need not be one which discourages species 22 from leaving droplets 14, nor be one which is substantially immiscible with the first fluid. Thus, by using an approach such as the one discussed above, first species 18 may be introduced into rigidified droplets 14 to form a first group 26 of species-containing droplets 22. This process can also be repeated for the second group 12 of rigidified droplets 16 (e.g., at least one second species 20 may be added to at least some of the second group 12 of rigidified droplets 16 to form a second group 28 of species-containing droplets 24).

In some cases, droplets from one or more of these groups may be combined together, e.g., to form a library. As an example, at least one rigidified droplet from the first group and at least one rigidified droplet for the second group may be combined to form a suspension of rigidified droplets 30, as indicated by arrow 11. Of course, this process can be repeated any number of times, e.g., 3, 4, or more times with different species, e.g., to form a library of droplets containing varying species.

Optionally, the rigidified droplets 30 (which may contain species such as first species 18 and/or second species 20) may be fluidized to form fluidized droplets 32, as indicated by arrow 13 in FIG. 1. The droplets may be fluidized, for example, by causing the droplets to undergo a phase change, e.g., by the temperature of the droplets, or by a chemical reaction. For instance, rigidified droplets containing agarose may be heated to a temperature above its gelling temperature.

The rigidified and/or the fluidized droplets may then be manipulated using any suitable technique, depending on the application. For instance, the droplets may be identified, sorted, separated, split, fused or coalesced, mixed, charged, sensed, determined, etc., using various systems and methods such as those disclosed in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/885,306, filed Aug. 29, 2007, entitled "Method and Apparatus for Forming Multiple Emulsions," by Weitz, et al.; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference.

As an example, the fluidized droplets shown in the example of FIG. 1 may be fused with droplets 40. As shown in FIG. 1, droplets 34 and droplets 36 may be combined to form a population of droplets 32 (some of which contain first species 18 and some of which contain second species 20, etc.), and the population of droplets are then fused with a plurality of droplets 40, as indicated by arrow 15. As a particular example, in some instances, each of the plurality of droplets 40 comprises at least one analyte molecule 44 that one of first species 18 and second species 20 may be able to interact with. In this example, each of the fused fluidic droplets 48, formed after fusing each of droplets 40 with one of droplets 18 or 20, will comprise at least one analyte molecule 44 and at least one of first species 18 or second species 20.

The plurality of microfluidic droplets may be analyzed, using a variety of techniques, to determined the at least one analyte. Examples of such techniques include, but are not limited to, those described in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006;

U.S. patent application Ser. No. 11/885,306, filed Aug. 29, 2007, entitled "Method and Apparatus for Forming Multiple Emulsions," by Weitz, et al.; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference.

It should be understood that the present invention is not limited to only the methods described above. In various aspects, various species can be loaded into fluidic droplets, e.g., to form a library of species, and the fluidic droplets can be made rigid or made fluid, for instance, to facilitate loading of species within the droplets, or to manipulate the species contained within the droplets. Accordingly, it should be noted that any combination of the above steps and/or additional steps may be used in the present invention, as discussed herein. For example, a plurality of rigidified droplets may be fused with a plurality of microfluidic droplets without the step of fluidizing the plurality of rigidified droplets. As another example, each group of rigidified droplets may also comprise at least one distinguishable identification element. As yet another example, the plurality of rigidified droplets may be separated into at least about 4096 groups. Each of the steps and/or additional steps are discussed in detail herein, as well as numerous examples of the combination of steps that may be performed.

In some embodiments of the present invention, a droplet, such as a microfluidic droplet, may be caused to undergo a phase change from a first phase to a second phase, which as mentioned above, may facilitate the loading of a species within the droplet and the like. Non-limiting examples of phases include solid phase, gel phase, liquid phase, gas phase, and the like. For example, a droplet may undergo a phase change from substantially liquid (e.g., the droplet is mostly in a liquid phase) to substantially solid (e.g., the droplet is mostly in a solid phase), or from substantially liquid to a substantially gel phase. It is important to note, however, that a phase change does not necessarily need to be a full change between two phases. For instance, a liquid droplet may be at least partially rigidified to form a rigidified droplet or vice versa.

A "rigidified droplet," as used herein, is a droplet that is in a state that is not fluid, e.g., the droplet is not in a liquid or gaseous state. For example, a rigidified droplet may be a solid droplet (e.g., a particle), a gel droplet, and the like. Materials that may be used to produce a rigidified or fluidized droplets, as well as methods to induce a phase change of a droplet are discussed more herein. As mentioned, in some cases, a rigidified droplet can be produced by causing a phase change in a fluidic droplet. Non-limiting examples of phase changes of a droplet that is rigidified include substantially gas phase to substantially solid phase, substantially gas phase to substantially gel phase, substantially liquid phase to substantially gel phase, substantially liquid phase to substantially solid phase, or the like. Non-limiting examples of phase changes of a droplet that is fluidized include substantially solid phase to substantially liquid phase, substantially gel phase to substantially liquid phase, or the like.

As mentioned above, in some embodiments, a species may be internally contained in a rigidified droplet, such as a microfluidic droplet. The species may be contained within the droplet during the initial formation of the droplet, or after the droplet has formed. In one set of embodiments, a droplet is first rigidified, and then exposed to a fluid containing the species. The species may enter the droplet, for example, via diffusion. The species may then be contained within the droplet, for instance, by chemically reacting the species to the droplet, or by replacing the fluid with a second fluid that does not allow the species to substantially leave the droplet (e.g., due to a difference in hydrophobicity or hydrophilicity).

The following discussion gives non-limiting examples of methods to add at least one species to a rigidified droplet. In other cases, the species may be added to the droplet by injecting the species into the droplet. In yet another case, the species may be a part of the first fluid, such that the species is present in the droplet (e.g., in the fluid) before the droplet is formed, rigidified and/or fluidized. Other methods and techniques for internally containing a species in a rigidified droplet will be known to those of ordinary skill in the art. In some embodiments, exposing a droplet to a fluid comprising a plurality of species may cause at least one species to be contained internally in the droplet. This may be achieved, in some cases, when the first fluid contained in the droplet and second fluid substantially surrounding the droplet are substantially miscible, and the second fluid comprises a plurality of a type of species. At least a portion of the fluid contained in the droplet and the fluid surrounding the droplet may exchange and cause at least one species to be contained internally within the first droplet.

Without wishing to be bound by theory, the substantial miscibility of the first fluid contained in the droplets and the second fluid surrounding the droplet may allow for this exchange in some cases. For example, when second fluid comprising at least one species is exchanged with at least some of the first fluid contained in the droplet, species comprised within the second fluid may also be transferred and contained internally within the droplet. In embodiments where the first fluid comprised within the rigidified droplet and the fluid surrounding the droplet are substantially immiscible, the first fluid contained within the droplet may not substantially exchange with the fluid substantially surrounding the droplet.

Figure 2A:
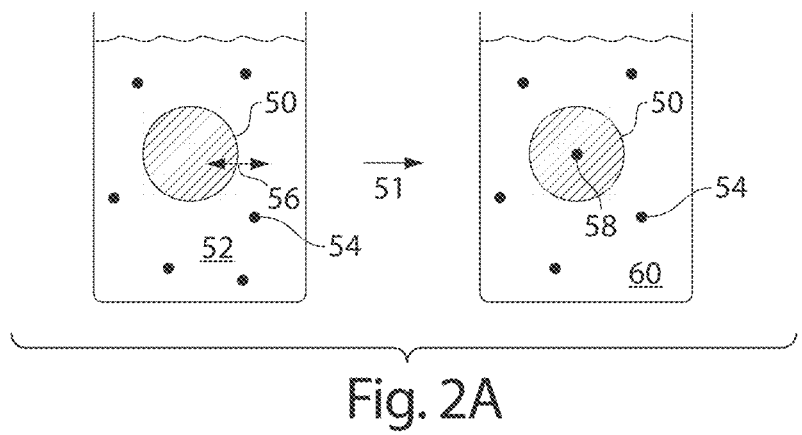
FIGS. 2A and 2B depict non-limiting embodiments of the exchange of fluids that may occur between a droplet and the fluid substantially surrounding the droplets, according to some embodiments of the present invention.
Figure 2B:
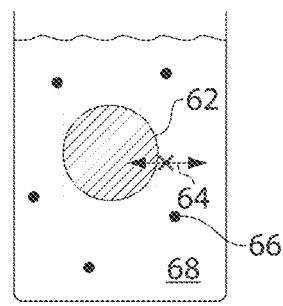

A non-limiting illustration of this exchange is depicted in FIG. 2. In FIG. 2A, a rigidified droplet 50 containing a first fluid is substantially surrounded by second fluid 52 comprising a plurality of species 54. First fluid 50 and second fluid 52 are substantially miscible in this example, and fluid exchange between the rigidified droplet and the second fluid may occur, as indicated by arrow 56. At least one of plurality of species 58 may be transferred into rigidified droplet 50 during the fluid exchange and the fluid surrounding the droplet 60 will now comprise the second fluid and at least some of the first fluid that was contained in the rigidified droplet 50. As another example, as shown in FIG. 2B, a rigidified droplet 62 containing a first fluid is substantially surrounded by second fluid 69 comprising a plurality of species 66. First fluid 60 and second fluid 62 are substantially immiscible and fluid exchange does not occur between the rigidified droplet and the second fluid, as indicated the cross through arrow 64.

Figure 6A:
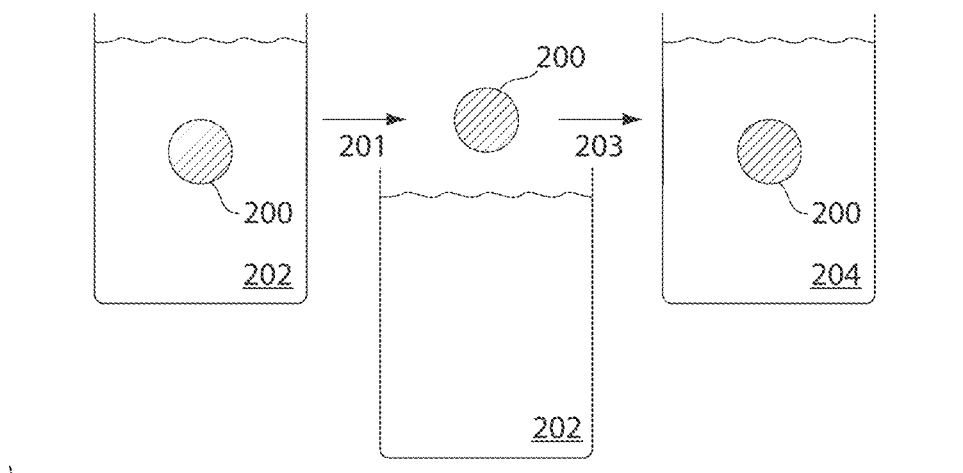
FIGS. 6A-6C show various methods for exposing a droplet of the present invention to a fluid.

A rigidified droplet comprising a first fluid and surrounded by a second fluid, may be exposed to a third fluid (e.g., comprising a plurality of a type of species) using any technique known to those of ordinary skill in the art. For example, the rigidified droplet may be removed from the second fluid and transferred to the third fluid, as depicted in FIG. 6A. In this figure, rigidified droplet 200 is substantially surrounded by second fluid 202. The rigidified droplet may be removed (e.g., removed using a pipette, tweezers, a spoon, vacuum, etc.) from second fluid 202, as indicated by arrow 201. Rigidified droplet 200 may then be added to third fluid 204, as indicated by arrow 203.

Figure 6B:
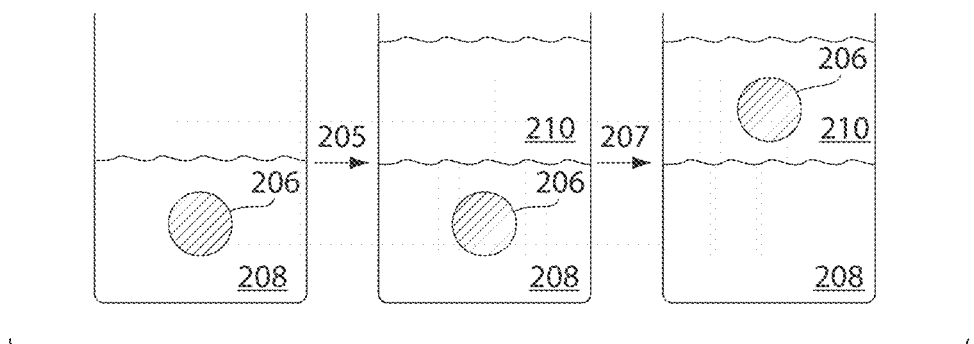

As another example, a third fluid may be added to the second fluid, and in instances where the second fluid and the third fluid are substantially immiscible, the third fluid and the second fluid may form one or more layers. The rigidified droplet may then be substantially surrounded the third fluid. An example of this process for replacing the second fluid with a third fluid is depicted in FIG. 6B. Rigidified droplet 206 is substantially surrounded by second fluid 208. Third fluid 210 may be added to second fluid 208. If second fluid 208 and third fluid 210 are substantially immiscible, third fluid 210 will form a layer above (as indicated by arrow 205) or below second fluid 208 (not shown). Rigidified droplet 206 may then be substantially surrounded by fluid 210, as indicated by arrow 207. The second and/or third fluid may be agitated (e.g., stirred, centrifuged, etc.) to aid in the exposure of the rigidified droplet to the third fluid.

Figure 6C:
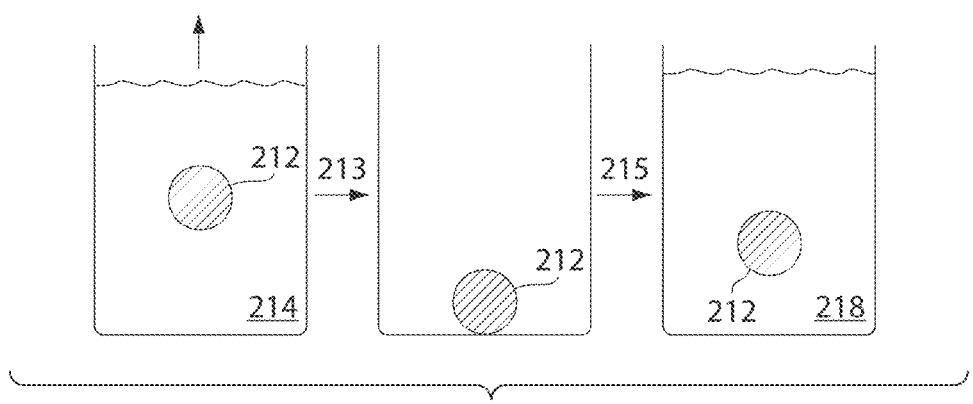

In yet another example, the second fluid may be removed from substantially surrounding the droplets (e.g., evaporation of the second fluid, aspiration or decanting of the second fluid, etc.), as depicted in FIG. 6C. Rigidified droplet 212 is substantially surrounded by second fluid 214 in this example. Second fluid 214 is then removed (e.g., draining of the second fluid) from substantially surrounding the rigidified droplet, as indicated by arrow 213. Third fluid 218 can then be provided and substantially surround rigidified droplet 212, as indicated by arrow 215. In some cases, the rigidified droplets may move into the third fluid, e.g., via gravity or differences in buoyancy.

In some embodiment, after a species has been contained internally in a rigidified droplet, the species may be immobilized relative to the rigidified droplet. Those of ordinary skill in the art will be aware of methods to immobilize a species with respect to a composition (e.g., gel, polymer) of a rigidified droplet. The species may be immobilized with respect to the composition of the droplet either directly (e.g., formation of a bond, such as a covalent bond) or indirectly (e.g., using a crosslinking molecule). In some instances, application of light or heat to a rigidified droplet internally containing a species may cause the species to become immobilized relative to the rigidified droplet. As another example, the species may be immobilized by exposure to a immobilizing agent (e.g., a chemical compound).

In some cases, more than one species of a single type will be contained internally in a rigidified droplet. For example, at least about 2 species, at least about 3 species, at least about 5 species, at least about 10 species, at least about 20 species, at least about 50 species, at least about 100 species, and the like, may be added to a rigidified droplet. In some instances, more than one type of species will be contained in the rigidified droplet. That is, at least one of a first type of species and at least one of a second type of species may be added to a rigidified droplet. This may be accomplished, for example, using the above techniques, where the fluid substantially surrounding the droplet (which may be substantially miscible with the fluid contained within the droplet) comprises a plurality of the first type of species and a plurality of the second type of species. The total number of a species in each of a plurality of droplets may or may not necessarily be equal. For example, a first droplet in a plurality of droplets may comprise only one species of a single type and second droplet in the plurality of droplets may comprise more than one species of a single type.

In some cases, a rigidified droplet may comprise at least about 2 types, at least about 3 types, at least about 4 types, at least about 5 types, at least about 6 types, at least about 8 types, at least about 10 types, at least about 15 types, at least about 20 types, or the like, of species. The total number of species of each type contained within the droplet may or may not necessarily be equal. For instance, in some cases, when two types of species are contained within a droplet, there may be approximately an equal number of the first type of species and the second type of species contained within the rigidified droplet. In other cases, the first type of species may be present in a greater or lesser amount than the second type of species, for example, the ratio of one species to another species may be about 1:2, about 1:3, about 1:4, about 1:5, about 1:6, about 1:10, about 1:20, about 1:100, and the like. The number of species of each type of species in each of a plurality of droplets in a group may or may not be equal. For example, a first droplet of a group may comprise one species of a first type and one species of a second type where a second droplet of the group may contain more than one species of the first type and one or more species of the second type.

The species may or may not be substantially soluble in the fluid contain in the droplet and/or the fluid substantially surrounding the droplet. For example, in some cases, a species may be substantially soluble in a second fluid substantially surrounding a droplet and in a first fluid contained within a droplet. In other cases, the species is substantially soluble in the second fluid and substantially insoluble in the first fluid, such that the species may precipitate when contained in the droplet. In yet other cases, the species is substantially insoluble in both the second fluid and the first fluid, and is suspended in the fluids.

The methods for forming a plurality of species-containing droplets and/or a suspension of rigidified species-containing droplets may be, in some embodiments of the present invention, applied to creating libraries of droplets containing various species. For example, in some embodiments, a plurality of rigidified droplets may be separated into at least a first group and at least a second group of rigidified droplets, where a distinguishable type of species may be contained internally in at least some of each group of droplets. At least one droplet from each group may be combined to form a plurality of droplets, each comprising at least one distinguishable species (e.g., a library of droplets) That is, at least one first species and one least second species may be added to at least a portion of the first group and the second group of rigidified droplets, respectively, and at least one droplet from each group may be combined to form a suspension of rigidified droplets (e.g., a library). Addition of a species to a droplet may be accomplished using any of the techniques discussed herein. In a particular embodiment, a first group of droplets and a second group of droplets are exposed to a first fluid and a second fluid comprising a plurality of a first species and a second species, respectively. The plurality of rigidified droplets may be separated into at least about 2 groups, at least about 4 groups, at least about 10 groups, at least about 30 groups, at least about 50 groups, at least about 64 groups, at least about 128 groups, at least about 1024 groups, at least about 4096 groups, at least about 10,000 groups, and the like. The number of groups the plurality of droplets is separated into may be selected such that the number is approximately equal to the total number of types of distinguishable species to be added to the droplets.

In some embodiments, a suspension may be formed that comprises at least a portion of each group of rigidified droplets. For example, a portion of a first group and of a second group of rigidified droplets may be suspended in a fluid. The first and second groups of rigidified droplets may be combined into a common suspension of the first and second groups of droplets using any known technique. For example, a first fluid comprising the first group of rigidified droplets and the second fluid comprising the second group of rigidified droplets may be combine to form a third fluid (e.g., comprising the first and the second fluids) comprising the first group and the second group of rigidified droplets. In some cases, only a portion of the first fluid comprising a portion of the first group of rigidified droplets will be combined with a portion of the second fluid comprising a portion of the second group of rigidified droplets. The first fluid and the second fluid may or may not comprise substantially the same make-up. In certain aspects, the first fluid and the second fluid will be miscible. In some cases, the suspension of rigidified droplets may be exposed to a third fluid using the techniques discussed here (e.g., see FIG. 6).

A suspension of rigidified droplets (e.g., a library of rigidified droplets) may be stored for any length of time. In some cases, the suspension of rigidified droplets may be stored such that the species contained within each droplet does not substantially change. That is, the species contained within each droplet do not diffuse from the droplet and/or new species are not contained internally in the droplet. Without wishing to be bound by theory, this aspect of the invention may be important during the formation of a library comprising labels. For example, if a label contained in a first droplet is able to exchange with a label contained in a second droplet, where the labels are each associated with a particular species in a library, the labels would be rendered useless in determining the species of the library contained in the droplet if exchange is possible. For example, at least about 100%, at least about 99.5%, at least about 99%, at least about 98%, at least about 97%, at least about 96%, at least about 95%, at least about 90%, at least about 85%, at least about 80%, and the like, of the plurality of rigidified droplets contained in the suspension may contain the same species after storage as they did prior to storage. The suspension of the droplets may be stored without substantial change for at least about 1 day, at least about 2 days, at least about 5 days, at least about 10 days, at least about 1 month, at least about six months, at least about 1 year, at least about 2 years, at least about 5 years, and the like.

Prior to forming the suspension of droplets, in some embodiments, a group of droplets containing at least one species may be exposed to a fluid which does not comprise any species. Without wishing to be bound by theory, exposure of the group of rigidified droplets containing a species to a fluid which is substantially immiscible with the droplets may prevent the species contained within the droplet from being transferred to the fluid surrounding the droplets through fluid exchange (e.g., because the fluids are not miscible, the exchange of the two fluids will be little or none). For example, a group of rigidified droplets containing at least one species and a first fluid may be exposed to a second fluid that does not comprise a plurality of species, where the first fluid and the second fluid are substantially immiscible. The immiscibility of the first fluid with the second fluid may not allow for the species contained in the droplet to diffuse into the second fluid. In other instances, when the species are immobilized relative to the droplet, the group of rigidified droplets may be exposed to a fluid which is substantially immiscible or substantially miscible with the fluid contained in the droplet since the species are immobilized relative to the droplet, the species may not be able to diffuse into the fluid substantially surrounding the droplet.

In some embodiments, a plurality of microfluidic droplets may be formed, where each of the microfluidic droplets comprises at least one species-containing rigidified or fluidized droplet (e.g., from a library of droplets) and in some cases, at least one target analyte molecule. Within the microfluidic droplet, the target analyte molecule may interact with a species for the species-containing droplets, and in some cases, the interaction may be determined. In instances where the species-containing droplets are fluidized, the fluidized droplet and the analyte droplet may be fused to form a single droplet containing the fluids from both droplets. This may occur if the fluid within the analyte droplet and the fluid in the fluidized droplet are substantially miscible. In instances where the species-containing droplet is rigidified, the rigidified droplet may be contained within the analyte droplet. A plurality of rigidified droplets may be fluidized using the methods and techniques discussed herein.

In some cases, a plurality of microfluidic droplets (e.g., fused droplets) may be formed by fusing at least a portion of a plurality of species-containing droplets (e.g., a library of droplets) with a plurality of analyte droplets containing analyte molecules. An "analyte droplet" is a droplet which contains at least one fluid and at least one target analyte molecule. The plurality of species-containing droplets may be rigid of fluidic. At least a portion of the species-containing droplets (either rigidified or fluidized) may be fused with a plurality of analyte droplets using microfluidic techniques, such as those described in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/885,306, filed Aug. 29, 2007, entitled "Method and Apparatus for Forming Multiple Emulsions," by Weitz, et al.; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference.

Figure 3A:
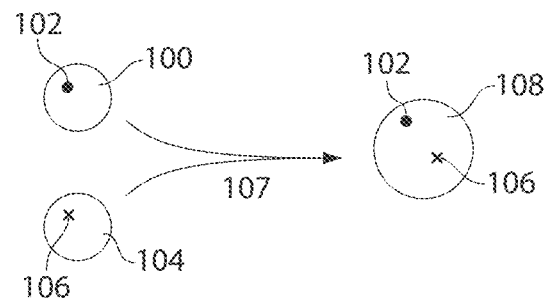
FIGS. 3A and 3B illustrate the fusing of an analyte droplet with a fluidized droplet or a rigidified droplet, respectively, to form a microfluidic droplet, according to some embodiments of the present invention.

In some cases, a plurality of fluidized species-containing droplets are fused with a plurality of analyte droplets. The fluid contained within the analyte droplet and the fluid contained within the suspensions of droplets, in most cases, may be substantially miscible. This may, in cases where the plurality of species-containing droplets are fluidized, allow for essentially complete fusion of a fluidized droplet with the analyte droplet, such that the fused microfluidic droplet formed contains the species from the fluidized droplet and the target analyte molecule. For example, as shown in FIG. 3A, fluidized droplet 100 from the suspension containing species 102 and analyte droplet 104 containing a target analyte molecule 106 are fused, as indicated by arrow 107, to form fused fluidic droplet 108 comprising species 102 and target analyte molecule 106.

Figure 3B:
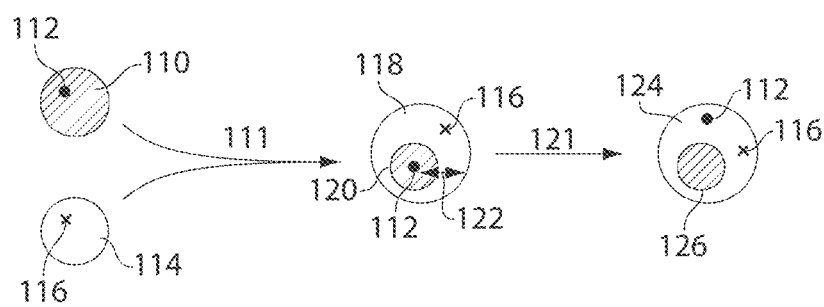

In other cases, the suspension of rigidified species-containing droplets are fused with a plurality of analyte droplets to form a plurality of fused microfluidic droplets. In some aspects of this embodiment, the fluid contained in the rigidified droplets may be substantially miscible with the fluid contained in the analyte droplet and may allow for the species contained within the rigidified droplet to diffuse from the rigidified droplet into the fluid of the fused microfluidic droplet, or for the target analyte molecule to be contained internally in the rigidified droplet, thus allowing the target analyte molecule and the species to interact. As a non-limiting example, as shown in FIG. 3B, species-containing rigidified droplet 110 containing species 112 and analyte droplet 114 containing target analyte molecule 116 are fused, as indicated by arrow 107, such that the fused microfluidic droplet formed 118 contains target analyte molecule 116 and rigidified droplet 120 containing species 112. The miscibility of the fluid contained in fused microfluidic droplet 118 and rigidified droplet 120 may allow for the exchange of fluid, as indicated by arrow 122. This may allow for species 116 to diffuse into the fluid of the fused droplet 124 from rigidified droplet 126, as indicated by arrow 121. In other aspects, a least a portion of the species contained in the rigidified droplet may remain contained internally in the rigidified droplet while interacting with the target analyte molecule.

In yet another embodiment, a plurality of species-containing rigidified droplets in which the species have been immobilized relative to a rigidified droplet may be fused with a plurality of analyte droplets. The interaction between the target analyte molecule and the species immobilized relative to a rigidified droplet may be determined. In such instances, the target analyte molecule may be substantially soluble in the fluid substantially surrounding the plurality of rigidified droplets. In addition, the fluid comprised in the rigidified droplets may be substantially miscible with the fluid substantially surrounding the droplets. Without wishing to be bound by theory, this property should allow for the target analyte molecule to diffuse into the rigidified droplet, thereby interacting with the species immobilized in the rigidified droplet.

Figure 3C:
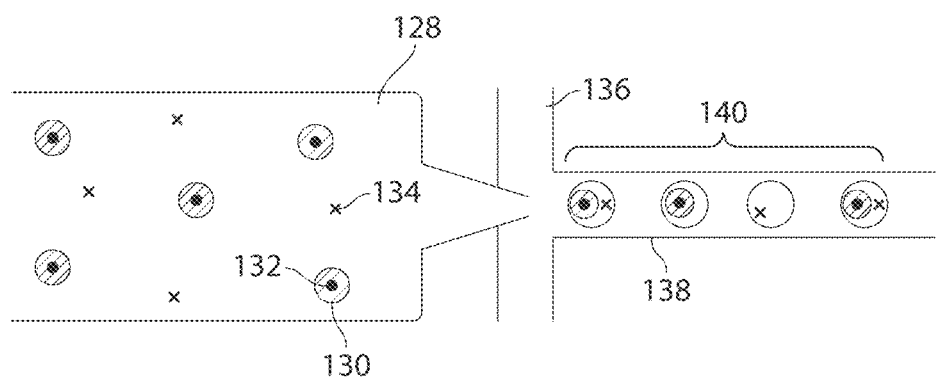
FIG. 3C illustrates the formation of a microfluidic droplet comprising a species and/or a target analyte molecule.

In still yet another embodiment, a plurality of microfluidic droplets may be formed using microfluidic techniques from a solution comprising a fluid, a suspension of rigidified species-containing droplets, and a plurality of target analyte molecules. For example, the plurality of target analyte molecules may be provided to the fluid substantially surrounding the plurality of rigidified droplets. Using microfluidic techniques, the fluid may be dispersed into droplets, where the dispersed droplets may comprise a target analyte molecule and/or a rigidified droplet. This non-limiting example is depicted in FIG. 3C. Fluid 128 is provided comprising a plurality of target analyte molecules 134 and a plurality of rigidified droplets 130 internally containing species 132. The continuous stream of fluid 128 may flow into microfluidic channel 138 comprising second fluid 136 to form a plurality of microfluidic droplets 140, a technique that will be well known to those commonly skilled in the art.

It should be understood when using the various embodiments discussed above, not every microfluidic droplet formed will comprise a rigidified or fluidized droplet and a target analyte molecule. Some droplets formed may contain neither a rigidified or fluidized droplet nor a target analyte molecule, some droplets formed may contain only one of the two, and some droplets formed may contain both. This by no means limits the applications of the droplets formed. Additional methods for forming a plurality and/or suspension of rigidified droplets are now described.

In one embodiment of the present invention, a method for forming a plurality of species-containing rigidified droplets comprising first providing a plurality of droplets, each of the plurality of droplets comprising a first fluid and being substantially surrounded by a second fluid, where the first fluid and the second fluid are substantially immiscible. The plurality of droplets may undergo a phase change to form a plurality of rigidified droplets (e.g., gel droplets). The plurality of rigidified droplets may be exposed to a third fluid, which may, in some cases, be substantially miscible with the first fluid contained in the rigidified droplets. At least one first species may be added internally to at least some of the rigidified droplets (e.g., by diffusion of a fluid containing the species into the droplet).

Figure 4:
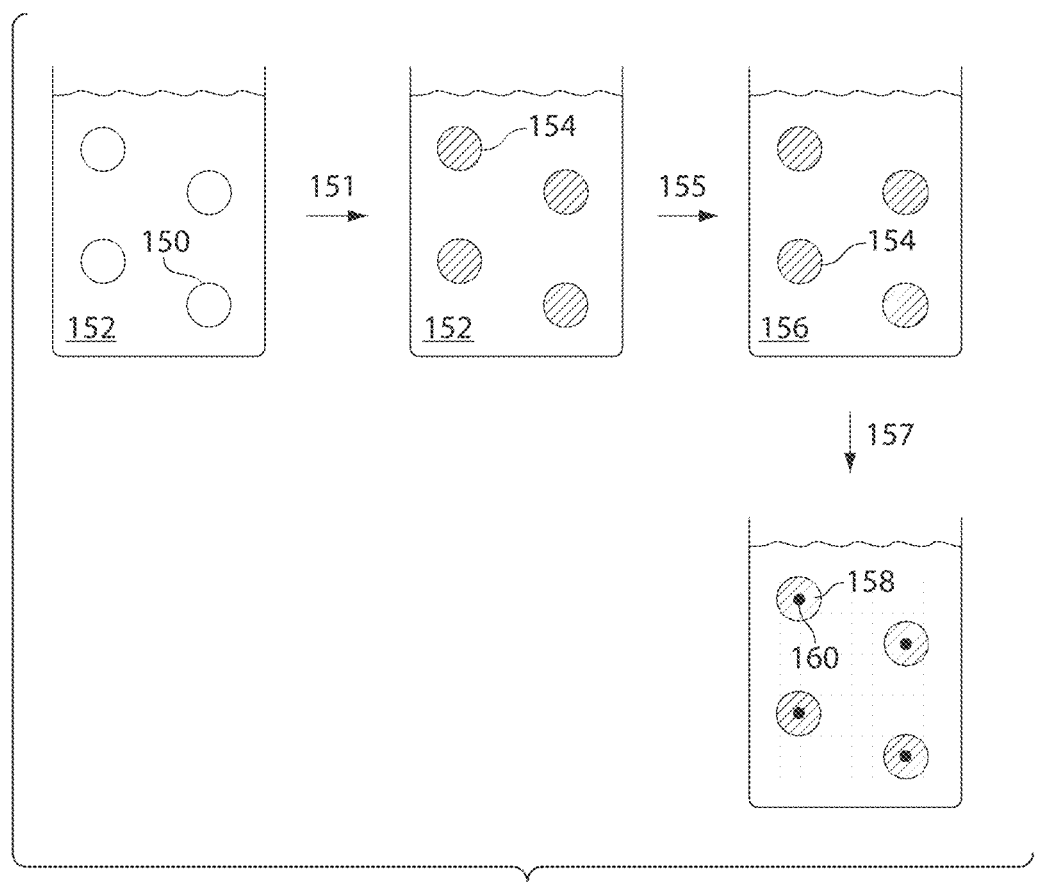
FIG. 4 illustrates a method for forming a plurality of rigidified droplets according to one embodiment of the present invention.

A non-limiting example of the above method is depicted in FIG. 4. A plurality of droplets 150 comprising a first fluid are substantially surrounded by a second fluid 152, where the first fluid and the second fluid are substantially immiscible. The plurality of droplets undergo a phase change, as indicated by arrow 151, to form a plurality of rigidified droplets 154, which are substantially surrounded by second fluid 152. The plurality of rigidified droplets 154 are exposed to a third fluid 156, where the first fluid comprised in the plurality of rigidified droplets 154 is substantially miscible with third fluid 156, as indicated by arrow 155. At least one first species 158 is added to each rigidified droplet 160, as indicated by arrow 157.

As another embodiment, a method to form a plurality of species-containing droplets may comprise the following steps. First, a plurality of groups of rigidified droplets may be provided. Each of groups of rigidified droplets may have substantially the same composition as the other groups of rigidified droplets, where each group of droplet contains the same first fluid and at least one distinguishable species with respect to the other groups of rigidified droplets. A suspension may be formed which contains at least one rigidified droplet from each of the groups of rigidified droplets. At least some of the suspension of droplets, in some cases, may be exposed to a second fluid, where the second fluid is substantially immiscible with the first fluid. Exposure of the rigidified droplets to a second fluid which is substantially immiscible with the first fluid contained in the droplets may allow for at least some of the droplets to be fluidized such that the droplets do not coalesce with the fluid surrounding the droplets.

Figure 5:
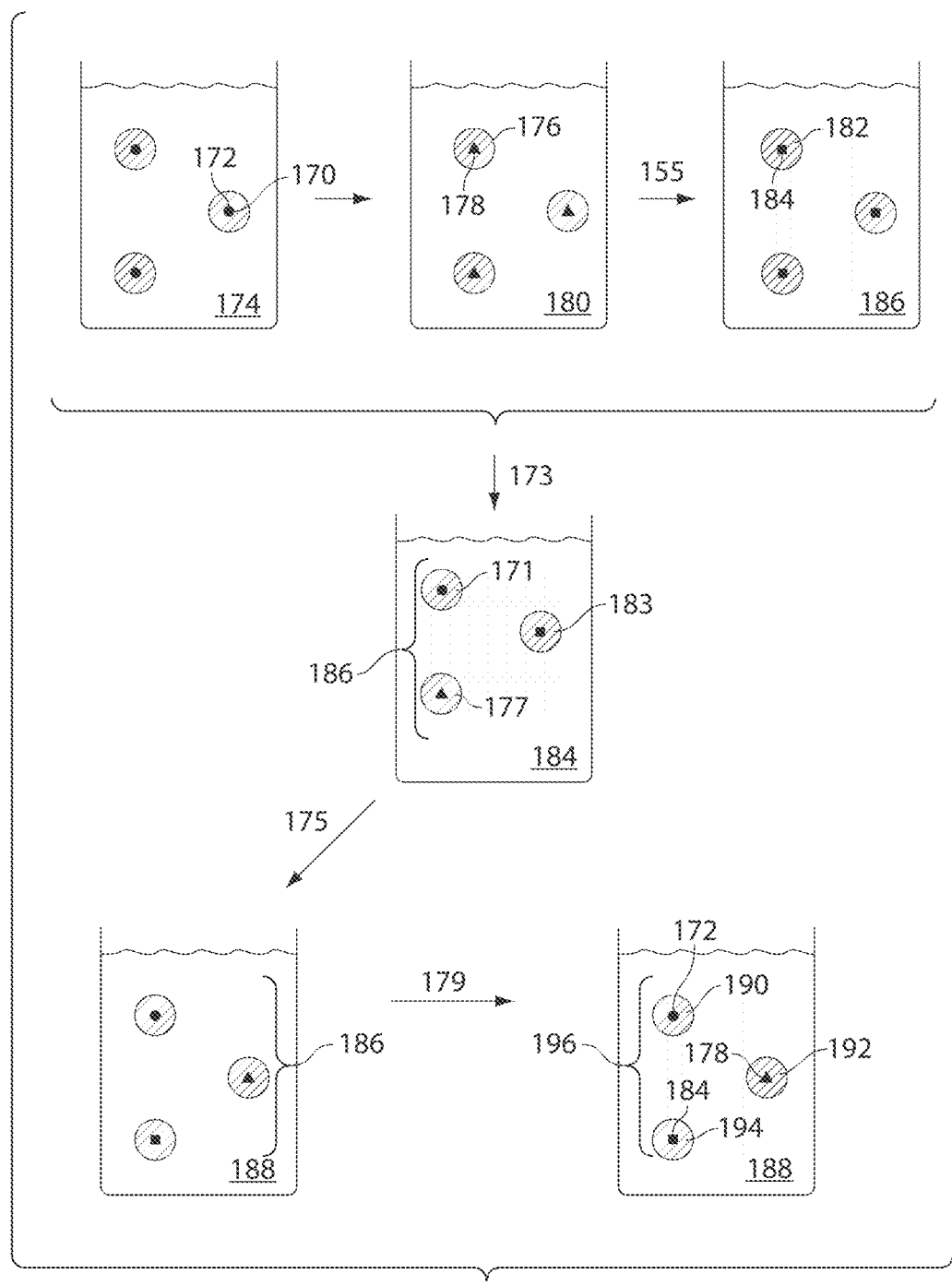
FIG. 5 depicts a method for forming a plurality of fluidized droplets comprising distinguishable species, according to some embodiments.

A non-limiting example is illustrated in FIG. 5. In this example, three groups of rigidified droplets (172, 176, 178) are provided, each droplet comprising a first fluid and at least one type of species (172, 178, 184, respectively), where each of the types of species are distinguishable with respect to the others species. Each of the groups of rigidified droplets are substantially surrounded by a second fluid (174, 180, 186), where the first fluids and the second fluids are substantially immiscible. Each of the groups of droplets have substantially the same make-up (e.g., each of the droplets consists essentially of the same material). The second fluid surrounding each of the groups of rigidified droplets may be the same or different fluid. A suspension 186 is formed which comprises at least one rigidified droplet from each of the three groups of droplets (171, 177, 183) suspended in fluid 184, as indicated by arrow 173. The suspension of droplets 186 may be exposed to a third fluid 188, as indicated by arrow 175. The suspension of droplets may then be fluidized, as indicated by arrow 179, to form a plurality of fluidized droplets 196 comprising a fluidized droplet from each group (190, 192, 194), each comprising a distinguishable species (172, 178, 184).

In yet another embodiment, the present invention provides a method for forming a suspension of species-containing droplets comprising at least one droplets from each of a first group of rigidified droplets and a second group of rigidified droplets, where the first group of rigidified droplets contains a first species which is distinguishable from the second species contained in the second group of rigidified droplets. The method may first provide a first plurality of rigidified droplets containing a first fluid, where each rigidified droplet is substantially surrounded by a second fluid which is substantially immiscible in the first fluid. The first plurality of rigidified droplets may be exposed to a third fluid, where the third fluid is substantially miscible in the first fluid. At least one first species may be added internally to at least some of the first plurality of rigidified droplets to form a first group of species-containing droplet. The above steps may be repeated with a second plurality of rigidified droplets and a second species to form a second group of species-containing droplets. A suspension may be then formed which contains at least some droplets of the first and second groups of species-containing droplets.

Figure 8:
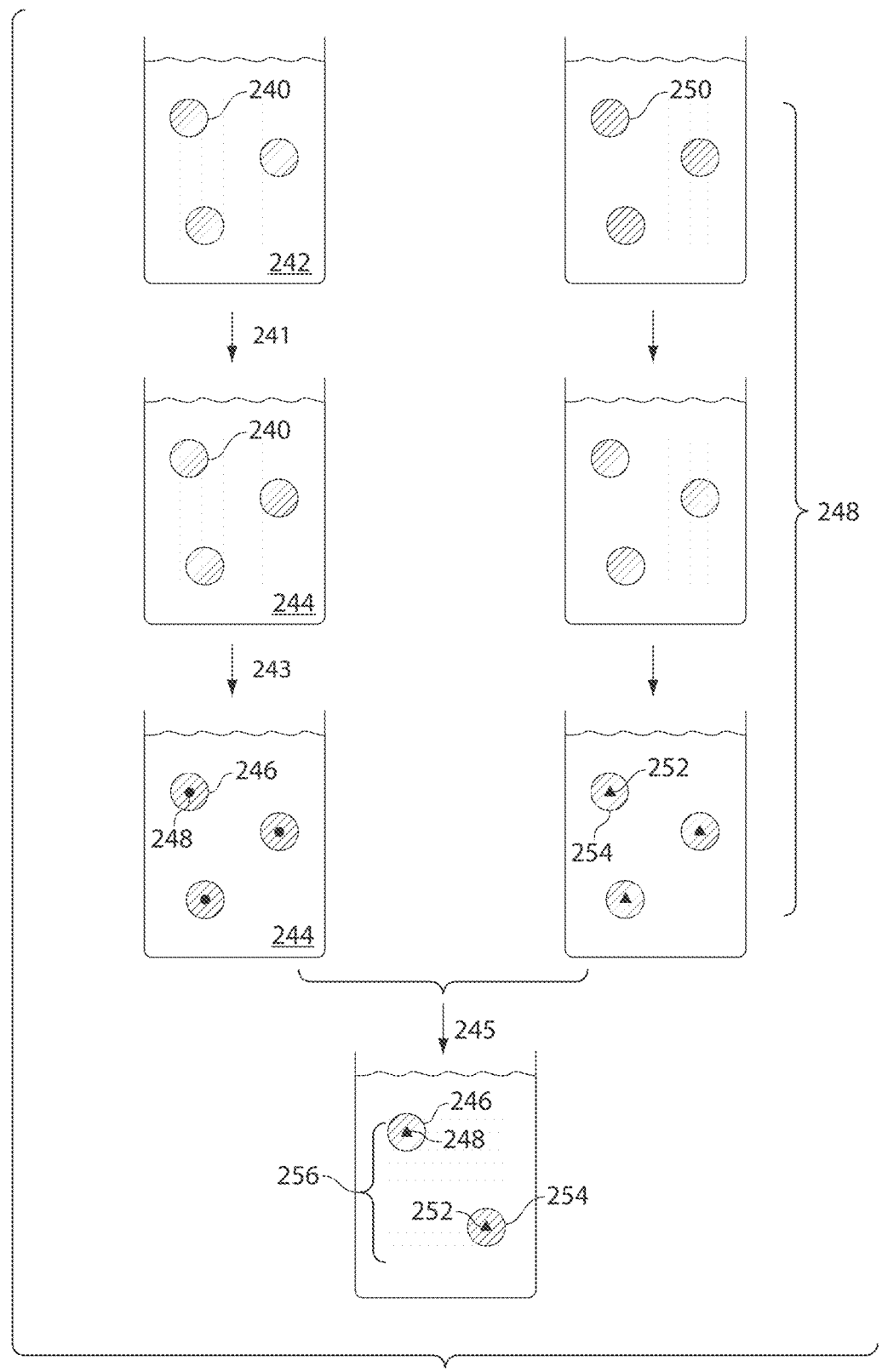
FIG. 8 illustrates a method for forming a plurality of rigidified droplets according to one embodiment of the present invention.

An example of the above is depicted in FIG. 8. A first plurality of rigidified droplets 240 comprising a first fluid is provided, where each of the rigidified droplets is substantially surrounded by a second fluid 242. The first plurality of rigidified droplets 240 are exposed to a third fluid 244, as indicated by arrow 241. A least one first species 248 is added to at least some of the first plurality of rigidified droplets to form a first group of species-containing droplets 248, as indicated by arrow 243. These series of steps 248 are performed with a second plurality of rigidified droplets 250, thereby forming a second plurality of species-containing droplets 254 comprising a second species 252, where first species 248 and second species 252 are distinguishable with respect to each other. A suspension 256 is then formed comprising at least one first species-containing droplet 246 and at least one second-species containing droplet 252, as indicated by arrow 245.

As mentioned above, the methods for forming a plurality of species-containing droplets and/or a suspension of rigidified species-containing droplets may be, in some embodiments of the present invention, applied to creating libraries of droplets containing various species. A library may contain droplets that are all substantially the same size and have substantially the same composition, but differ in the species contained within the droplets. For instance, a first member of a library may be a collection of droplets containing a first species, and a second member of a library may be a collection of droplets containing a second species, the first species at a different concentration, a first species and a second species, or the like. Such libraries may be useful, for example, for nucleic acid sequencing applications, screening assays, or the like.

In some cases, the library includes compositions comprising a container comprising a plurality of mutually distinguishable rigidified droplets, each having substantially the same composition but containing a distinguishable species with respect to the other rigidified droplets. In some cases, the composition is produced using the methods discussed herein. The composition may comprise at least about 5, at least about 8, at least about 10, at least about 20, at least about 50, at least about 64, at least about 100, at least about 128, at least about 200, at least about 500, at least about 1000, at least about 4096, at least about 10,000, at least about 50,000, and the like, mutually distinguishable species. The substantially same composition of the rigidified droplets may comprise a polymer and/or gel.

The composition and methods of the present invention may be useful for the sequencing of a target nucleic acid. For example, the target analyte molecule may be a nucleic acid and the species may be selected from a library of nucleic acid probes, such that the sequence of the nucleic acid may be determined. Other target analyte molecules that can be studied include, for example, biochemical species such as nucleic acids such as siRNA, RNAi and DNA, proteins, peptides, or enzymes. It should be understood, however, that while the discussion herein primarily focuses on the use of droplets of the present invention for sequencing a nucleic acid, this is by way of example only, and the droplets have many other uses, such as techniques relating to fields such as food and beverages, health and beauty aids, paints and coatings, and drugs and drug delivery. For example, in some instances, a target analyte molecule may be a cell, and the interaction of the cell with a variety of species (e.g., drugs, hormones, etc.) may be determined. Species that can be incorporated within droplets of the invention include, but are not limited to, nucleic acid probes, nanoparticles, quantum dots, fragrances, proteins, indicators, dyes, fluorescent species, chemicals, or the like. A droplet or emulsion can also serve as a reaction vessel in certain cases, such as for controlling chemical reactions, or for in vitro transcription and translation, e.g., for directed evolution technology. In addition, droplets of the present invention may comprise additional reaction components, for example, catalysts, enzymes, inhibitors, and the like.

In some embodiments, the target analyte molecule may be a target nucleic acid to be sequenced, where the target nucleic acid may be any suitable nucleic acid. For example, the target nucleic acid may be a nucleic acid that encodes a biological entity, such as a protein, an enzyme, an antibody, a receptor, a ribozyme, a ribosome, or the like, and/or a portion thereof. As another example, the target nucleic acid may be a regulatory sequence or a non-coding sequence, for instance, a small interfering RNA, a microRNA, a small hairpin RNA, or the like. The target nucleic acid can be any number of nucleotides in length, for example, on the order of 25, 50, 60, 64, 70, 80, 90, 100, 200, 400, 800, 1600, 3200, 6400, or even more nucleotides in length. Non-limiting examples of target nucleic acids include ribonucleic acid (RNA), deoxyribonucleic acid (DNA), or mixtures or copolymers thereof, which may be isolated from natural sources, recombinantly produced, artificially synthesized, etc. The nucleic acid may contain residues such as adenosine or "A," thymidine or "T," guanosine or "G," cytidine or "C," or uridine or "U," or other residues, such as the universal residues. The nucleic acid can be double-stranded or single stranded to facilitate hybridization. Moreover, the nucleic acid can be obtained from virtually any source. For instance, the nucleic acid may be isolated from a cell or a virus, synthesized using traditional chemical synthesis, synthesized using polymerase chain reaction (PCR) technology, or the like.

The target nucleic acid contained within the droplet may be exposed to a nucleic acid probe and/or one or more identification elements. For instance, as previously discussed, an analyte droplet comprising at least one target analyte molecule (e.g., a target nucleic acid) may be fused with a species-containing droplet (e.g., a nucleic acid probe) and in most cases, at least one identification element for determining the nucleic acid probe. The fluidic droplets may be used for sequencing a nucleic acid using techniques such as those disclosed in U.S. Patent Application Ser. No. 61/008,862, filed Dec. 21, 2007, entitled "Systems and Methods for Nucleic Acid Sequencing," by Weitz, et al, herein incorporated by reference.

The suspension of droplets (either fluidized or rigidified) may comprise a plurality of group of droplets, where each group of droplet internally contains at least one nucleic acid probe. Nucleic acid probes are generally used, in certain embodiments, to determine certain sequences within the target nucleic acid. Often, short portions of the target nucleic acid can be associated with the nucleic acid probe, for instance, a sequence of less than 20 residues, less than 15 residues, less than 10 residues, less than 9 residues, less than 8 residues, less than 7 residues, less than 6 residues, less than 5 residues, less than 4 residues, etc. The residues are typically contiguous within the target nucleic acid probe although, in some cases, some of the residues within the target nucleic acid are not necessarily contiguous. In some embodiments, a nucleic acid probe may contain a relatively short sequence of nucleic acid residues that is able to recognize at least a portion of the target nucleic acid, and often has a similar length as the recognized portion of the target nucleic acid. For instance, the nucleic acid probe may have a sequence having length of less than 20 nucleotides or less than 10 nucleotides in some cases, or a length such as those described above. In one case, the length of the nucleic acid probe sequence may be four residues (e.g., FIG. 7A). In another case, the length may be five residues (e.g., FIG. 7B). In yet another case, the length may be six residues (e.g., FIG. 7C). The nucleic acid probe sequences within the nucleic acid probe may be contiguous, or the sequence may be non-contiguous. For instance, there may be universal residues or gaps present. In some instances, the nucleic acid probe may be labeled in some manner, such as with a signaling entity, for instance, a radioisotope or with a fluorescence tag (e.g., FIG. 7D). Various signaling entities and other examples of nucleic acid probes will be discussed in more detail below.

The nucleic acid probe may be selected such that at least some of the probes will contain sequences complementary or substantially complementary to the target nucleic acid sequence. For instance, in one embodiment, the nucleic acid probe sequences are selected such that every permutation of nucleic acid residues of a certain size or number (or range of sizes or numbers) is represented, thereby ensuring that at least one of those nucleic acid probe sequences is substantially complementary to the target nucleic acid. As used herein, a first sequence that is "substantially complementary" to a second sequence is one which at least about 75% of the first and second sequences are complementary (e.g., through Watson-Crick complementarity pairing) and/or the sequences have a maximum of 1 or 2 base mismatches. In some embodiments, the two sequences may be at least about 80%, at least about 85%, at least about 90%, at least about 95%, at least about 97%, at least about 98%, at least about 99% or at least about 100% complementary.

In some embodiments, a plurality of distinguishable or non-identical nucleic acid probes is used, for example, nucleic acid probes having one or more differences in the sequence of residues contained within the nucleic acid probes. For instance, a plurality of fluidized or rigidified droplets may be used, and the droplets may each contain a specific nucleic acid probe sequence. The droplets may be prepared such that each droplet contains only one nucleic acid probe sequence (although multiple copies of the nucleic acid probe may be present). In addition, in some cases, different droplets may independently contain the same or different nucleic acid probe sequence (e.g., such that there is some redundancy so that not each droplet in a given population or collection of droplets is necessarily unique).

In some cases, the nucleic acid probe may be labeled, e.g., with a signaling entity. The signaling entity may be determined in some fashion using a detection method, such as those discussed herein. The signaling entity may be included within the nucleic acid probe at any suitable location, for example, at a 5' terminal site of the nucleic acid sequence of the nucleic acid probe, a 3' terminal site, or at an internal site within the nucleic acid probe. In some cases, the signaling entity may be chosen such that it produces a different signal (or does not produce a signal) when the nucleic acid probe is associated with a target nucleic acid compared to when the nucleic acid probe is not associated with the target nucleic acid. The signaling entity may include, but is not limited to, a fluorescent dye, a chemiluminescent entity, a radioactive label, an isotope such as a non-radioactive isotope or an isotope detectable by mass spectrometry (e.g., an electrophore mass label (EML)), a ligand which can serve as a specific binding partner to a labeled antibody, an enzyme, an antibody which can serve as a specific binding partner for a labeled ligand, an antigen, a group having a specific reactivity, and/or an electrochemically detectable moieties. Non-limiting examples of fluorescent signaling entities include fluorescein, rhodamine, or hexachlorofluorescein; those of ordinary skill in the art will be aware of other fluorescent entities that are readily commercially available. Yet other examples of signaling entities are discussed in detail herein.

For instance, in one embodiment, a nucleic acid probe can include a sequence of nucleic acid residues, a signaling entity, and a quencher or an enhancer (e.g., as is shown in FIG. 7E, with the signaling probe labeled S and a quencher labeled Q). The signaling entity may be, e.g., a fluorescent entity, and may be located anywhere in the nucleic acid probe, for instance, covalently attached to the 5' end of the nucleic acid sequence. Non-limiting examples of fluorescent entities potentially suitable for use in the nucleic acid probe in various embodiments include 6-carboxyfluorescein and tetrachlorofluorescin. The quencher or enhancer may be any entity able to affect the signaling entity in some fashion, e.g., by respectively inhibiting or facilitating determination of the signaling entity. For instance, the proximity of a fluorescent signaling entity and a quencher within a nucleic acid probe may be such that the quencher is able to partially or completely inhibit fluoresence of the signaling entity, while an enhancer may be able to enhance the fluorescence of a fluorescent signaling entity when the enhancer is positioned proximate the signaling entity. The quencher or enhancer may also be located anywhere in the nucleic acid probe, for example, attached to the 3' end of the nucleic acid sequence. Non-limiting examples of quenchers include tetramethylrhodamine and dihydrocyclopyrroloindole tripeptide.

As a non-limiting example, a quencher (or similarly, an enhancer) can be used within a signaling entity in a nucleic acid probe as follows. A nucleic acid probe associated with a target nucleic acid may be removed or dissociated from the target nucleic acid by the action of certain enzymes or other species, for instance, polymerases such as Taq polymerases. For instance, in some cases, a polymerase may cause degradation of the nucleic acid sequence within the nucleic acid probe to occur, which may cause release of the signaling entity and/or the quencher or enhancer and hence, the quencher or enhancer may no longer be proximate to or at least substantially affect the signaling entity. Thus, degradation of the nucleic acid probe can be determined by determining a change in the signaling entity. In contrast, in systems where the nucleic acid probe does not sufficiently associate with the target nucleic acid (e.g., if no sufficiently complementary sequences are present), no degradation of the nucleic acid probe would occur through action of the polymerase or other species (e.g., any association that exists between the target nucleic acid and the nucleic acid probe is too transient or short for enzymatic action to occur), and thus, no significant change in the signal of the signaling entity could be determined. Accordingly, in one embodiment, a polymerase such as Taq polymerase may be provided to a fluidic droplet comprising a nucleic acid probe and a target nucleic acid. The polymerase may be provided to the fluidic droplet using any suitable technique, as discussed herein.

In some cases, a nucleic acid probe may comprise at least one locked nucleic acid (LNA) residue (see, e.g., FIG. 7F). A locked nucleic acid residue is a nucleic acid analog that has a chemical shape similar to a naturally occurring nucleic acid residue (e.g., being able to form 2 or 3 hydrogen bonds with a complementary residue), but is not free to rotate in as many dimensions as a naturally occurring nucleic acid residue. For instance, in some cases, a locked nucleic acid residue may contain a 2'-O, 4'-C methylene bridge, where the methylene bridge "locks" the ribose in the 3'-endo structural conformation, which is often found in the certain form of DNA or RNA. The locked ribose conformation may enhance residue stacking and/or backbone pre-organization. This can significantly increase the thermal stability (melting temperature) of the nucleic acid sequence in some cases. A nucleic acid probe containing one or more locked nucleic acid residues may be useful in certain embodiments because the locked nucleic acid residue may exhibit increased affinity for association with the target nucleic acid, e.g., due to the restrictions on its ability to internally rotate.

In certain embodiments, the nucleic acid probe may contain a universal residue, which may be able to engage in a residue-pairing relationship with more than one natural nucleotide, and in some cases, with all of the natural nucleotides. Exemplary universal residues include 5-nitroindole and 3-nitropyrrole, although other universal residues useful for the systems and methods described herein will be known to those of skill in the art. As discussed below, a nucleic acid probe containing one or more universal bases may be useful in certain embodiments.

The nucleic acid probes may be synthesized using any suitable technique, e.g., solid phase phosphoramidite triester methods. In some cases, a plurality of nucleic acid probes is synthesized, forming a library of such probes. The library may include a plurality of sequences, for example, organized in a plurality of droplets. In some (but not all) embodiments, the library may contain sequences that have roughly the same number of residues, for example, around 4 residues, around 5 residues, around 6 residues, around 7 residues, etc. The library of nucleic acid probes may be prepared using any suitable technique, and may be produced using manual techniques or automated, e.g., using a robotic apparatus.

In one embodiment, the library may comprise every possible sequence for a set of nucleic acid sequences having a certain length or lengths. In another embodiment, the library may comprise at least about 30%, at least about 50%, at least about 80%, at least about 85%, at least about 90%, at least about 95%, or at least about 100% of all possible sequences having a certain length or lengths. Some techniques for preparing a library are discussed below.

The library of nucleic acid probes (or any other species) may be internally contained within droplets of the present invention using any suitable technique, as discussed herein. For example, a plurality of rigidified droplets may be produced microfluidically, such that the plurality of rigidified droplets have substantially the same composition as all other droplets of the present invention. A library of nucleic acid probes may be provided (e.g., prepared on a microtiter plate using a robotic apparatus), where each type of distinguishable nucleic acid probe is kept separate from all other types nucleic acid probes. A plurality of rigidified droplets may be separated into approximately the same number of groups as there is types of nucleic acid probes, and each group of rigidified droplets may be exposed to one type of nucleic acid probe, such that at least one of each type of nucleic acid probe is contained internally in a rigidified droplet, forming a plurality of groups of distinguishable droplets (e.g., each group containing a distinguishable nucleic acid probe). At least one of each type of rigidified droplet containing interally a distinguishable nucleic acid probe may be combined to form a suspension off rigidified droplets.

In many embodiments, at least one identification element may also be contained internally in each group of fluidized or rigidified droplets. An "identification element" as used herein, is a species that includes a component that can be determined in some fashion, e.g., the identification element may be identified when contained within a droplet. The identification elements may be insoluble (e.g., suspended) or soluble within the droplet. Non-limiting examples include identification elements detectable by fluorescence, chemiluminescence, radioactivity, or the like. Specific examples include, but are not limited to, particles containing dyes, quantum dots, or fluorescent particles which, in some embodiments, may also have other species attached thereto, for instance, oligonucleotides such as those described herein. In some cases, more than one identical identification element may be present within any given droplet.

In certain embodiments, more than one non-identical identification element may be used, e.g., within a droplet. For instance, a droplet may contain at least two distinguishable identification elements, at least three distinguishable identification elements, at least four distinguishable identification elements, at least five distinguishable identification elements, etc. Identification elements may be distinguished using any suitable method, e.g., color, fluorescence, absorption, intensity, size, charge, radioactivity, mass, or the like.

In one set of embodiments, particles or microparticles (e.g., beads) may be used as identification elements. The particles may have any dimension, and may be spherical or non-spherical. For instance, the particles may have average diameters ranging from approximately 100 nm to 100 um in diameter in some cases. In certain embodiments, the particles may have an average diameter of less than about 1 micrometer, less than about 300 nm, less than about 100 nm, less than about 30 nm, or less than about 10 nm. The average diameter, as used herein, is the arithmetic average of the diameters of the particles contained within the droplets. The diameters of a non-spherical particle is the diameter of a perfect mathematical sphere having the same volume as the particle.

In some embodiments, a plurality of identification elements may be chosen to identify droplets such that there are at least 3 distinguishable identification elements, at least 4 distinguishable identification elements, at least 6 distinguishable identification elements, at least 8 distinguishable identification elements, at least 9 distinguishable identification elements, at least about 10 distinguishable identification elements, at least about 20 distinguishable identification elements, at least about 30 distinguishable identification elements, at least about 40 distinguishable identification elements, at least about 50 distinguishable identification elements, at least about 60 distinguishable identification elements, at least about 70 distinguishable identification elements, at least about 80 distinguishable identification elements, at least about 90 distinguishable identification elements, at least about 100 distinguishable identification elements, etc. One non-limiting example of a plurality of distinguishable identification elements are the Luminex FlexMAP Microspheres beads commercially available from Luminex Corp. Beads or particles such as these may be distinguished, according to one embodiment, by the use of two or more dyes or other compounds that can be independently varied within each bead or particle. Therefore, a plurality of distinguishable beads may be used as a plurality of identification elements, according to certain embodiments. As another, specific non-limiting example, particles comprising polystyrene and one or more dyes may be used as identification elements. The dyes employed within the particles may include, for instance, squaric acid-based molecules or other fluorescent molecules that exhibit fluorescence, e.g., extending into near infrared and/or infrared region. In some cases, two or more dyes with concentrations that can be independently controlled can be used within each particle.

The sequence of a target nucleic acid may be determined by determining the association (or non-association) of the target nucleic acid to one of a plurality of distinguishable nucleic acid probes. The target nucleic acid may be associated with the nucleic acid probe when they form a relatively stable duplex by hydrogen bonding under experimental conditions. Relatively stable hydrogen bonding may be formed due to Watson-Crick complementarity (e.g., A matches T, but not G or C; G matches C, but not A or T) and/or other effects such as GC wobble, or other associations caused by locked nucleic acids or universal bases, as discussed herein. Non-limiting examples of suitable methods for determining the sequence of a target nucleic acid include sequencing by hybridization techniques that are known to those of ordinary skill in the art.

Sequencing by hybridization (SBH) is a method for examining the nucleic acid residue sequence in a target nucleic acid that has been previously described, for instance, in U.S. Pat. No. 5,202,231. In general, SBH uses a set of nucleic acid probes of defined sequence to probe for complementary sequences on a longer target strand of a target nucleic acid. The defined sequences which hybridize to the target can then be aligned using computer algorithms to construct the sequence of the target nucleic acid.

Thus, in one embodiment of the present invention, a target nucleic acid may associate with a certain combination of nucleic acid probes, leading to a characteristic "hybridization" pattern. Each positive association (or hybridization) event in a given sample provides a discrete piece of information about the target nucleic acid. In some cases the target nucleic acid may be sampled without determination of exactly where any particular nucleic acid probe associates with the target nucleic acid. Algorithms and software have been developed for target nucleic acid reconstruction, based on the hybridization pattern, and are known to those skilled in the art. In other cases, however, analysis of a hybridization pattern, such as those described herein, may provide a "fingerprint" identification of the target nucleic acid sequence, without specifically determining the target nucleic acid sequence itself. The pattern of hybridization may also be manually or computer analyzed.

Another aspect of the present invention is generally directed to systems and techniques for creating a suspension of rigidified or fluidized droplets, where the droplets contain distinguishable species and/or identification elements. In some embodiments, a plurality of distinguishable identification elements may be used to identify a plurality of fluidic droplets, and in some cases, the distinguishable identification elements are used to determine a nucleic acid sequence (e.g., of a nucleic acid probe) present within each droplet. For instance, in one embodiment, at least about 64, at least about 256, at least about 1024, at least about 4096, or at least about 16,384 or more fluidic droplets may be prepared, each containing a nucleic acid probe (including multiple copies of the nucleic acid probe) and one or more identification elements that, in combination, identifies that nucleic acid probe and do not identify different nucleic acid probes. The present invention provides, in one set of embodiments, systems, and methods for preparing such collections of fluidized or rigidified droplets.

In one embodiment, a plurality of distinguishable identification elements are used to identify a plurality of fluidic droplets or nucleic acid probes or other suitable samples. For instance, if fluorescent particles are used, a set of distinguishable particles is first determined, e.g., having at least 5 distinguishable particles, at least about 10 distinguishable particles, at least about 20 distinguishable particles, at least about 30 distinguishable particles, at least about 40 distinguishable particles, at least about 50 distinguishable particles, at least about 75 distinguishable particles, or at least about 100 or more distinguishable particles. A non-limiting example of such a set is available from Luminex. The distinguishable identification elements may be divided into a plurality of groups (e.g., 2, 3, 4, 5, 6, 7, or more), where each group contains at least two members of the set of distinguishable identification elements.

A sample may then be associated with one member chosen from each of the groups of distinguishable identification elements. For instance, a first sample may be identified by the combination of a first element chosen from a first group, a first element chosen from a second group, and a first element chosen from a third group, as each of these elements is distinguishable from each other; a second sample may be identified by the combination of a first element chosen from the first group, a first element chosen from the second group, but a second element chosen from the third group. The number of unique combinations, in this example, is simply the product of the number of members of each of the groups; a large number of distinguishable sets of identification elements can thus be prepared. Thus, for instance, by defining at least six identification elements, where the identification elements are arranged into at least three groups with each group having at least two identification elements, at least eight different samples can be determined by associating each of the at least eight samples with at least three of the identification elements, where each identification element associated with each sample is chosen such that there is one identification element from each of the at least three groups. Even larger numbers may be obtained by increasing the numbers of members in each group and/or the numbers of groups present. In addition, the number of members of each group may be the same, or different in some cases.

It should be noted that in other embodiments, other coding methods are also possible. For instance, the distinguishable elements may be used to represent binary digits, such that the nucleic acid probes or other samples are arbitrarily numbered and are identified by adding the binary digits corresponding to the distinguishable identification elements that are present.

Accordingly, in some embodiments, a species-containing droplet can be identified by introducing to the species-containing droplet, one or more identification elements that have been arranged in such a manner. Relatively large numbers of fluidic droplets can each be identified. For instance, a collection of tens, hundreds, or thousands of fluidic droplets, containing differing nucleic acid probes, may be identified by adding, to each of the droplets, three or four identification elements that have been determined in such a manner.

The composition of a plurality of droplets (e.g., fluidized, rigidified, and/or species-containing) will now be discussed. In some embodiments, droplets of the present invention comprise a precursor material, where the precursor material is capable of undergoing a phase change, e.g., to form a rigidified droplet or a fluidized droplet. Therefore, the droplet may be rigidified or fluidized by causing the precursor material to rigidify or fluidized. For instance, a droplet may contain a gel precursor and/or a polymer precursor that can be rigidified to form a rigidified droplet comprising a gel and/or a polymer. The rigidified droplet, in some cases, may also contain a fluid within the gel or polymer.

The rigidified droplet may be substantially porous or substantially non-porous. In some aspects, the rigidified droplet will be substantially porous such that at least one species may be contained internally within the rigidified droplet. As used herein, "contained internally" or "added internally" means that the species is substantially surrounded by the droplet. In other embodiments, however, a species may be contained within a non-porous droplet, or the species may be contained on the surface of the droplet (e.g., at an interface between the droplet and the fluid surrounding the droplet).

A droplet may be caused to undergo a phase change using any suitable technique. For example, a rigidified droplet may form a fluidized droplet by exposing the rigidified droplet to an environmental change. A droplet may be fluidized or rigidified by a change in the environment around the droplet, for example, a change in temperature, a change in the pH level, change in ionic strength, exposure to a electromagnetic radiation (e.g., ultraviolet light), addition of a chemical (e.g., chemical that cleaves a crosslinker in a polymer), and the like. Some examples are given below.

As a specific example, in some cases, a droplet may be caused to undergo a phase change by raising or lowering the temperature of the droplet from a first temperature to a second temperature. For example, a first temperature may be raised or lowered to a second temperature by at least about 5° C., at least about 10° C., at least about 15° C., at least about 20° C., at least about 22° C., at least about 25° C., at least about 30° C., at least about 35° C., at least about 40° C., at least about 50° C., at least about 60° C., at least about 70° C., at least about 80° C., at least about 90° C., at least about 100° C., or to any other suitable temperature that may cause the droplet to undergo a phase change. As an specific example, a fluidic droplet comprising agarose may be rigidified by cooling the droplet to a temperature below the gelling temperature of agarose, or a rigidified droplet comprising agarose may be fluidized by warming. In some cases, the temperature change is chosen in part such that a species (e.g., a cell) contained within the droplet remains unchanged. Non-limiting examples of gels that may form upon a change in temperature include agarose, a PEG-PLGA-PEG triblock copolymer, Matrigel, or the like.

As another example, a droplet may be caused to undergo a phase change by raising or lowering the pH of the droplet from a first pH to a second pH. For example, a first pH may be raised or lowered to a second pH by at least about 0.5 pH units, at least about 1 pH unit, at least about 2 pH units, at least about 3 pH units, at least about 4 pH units, at least about 5 pH units, at least about 6 pH units, at least about 8 pH units, at least about 10 pH units, at least about 14 pH units, or to any other suitable pH that may cause the droplet to undergo a phase change. In some cases, the pH of the droplet may be changed from acidic to basic, basic to acidic, less acidic to more acidic, more acidic to less acidic, more basic to less basic, less basic to more basic, and the like. Non-limiting examples of gels that may undergo a phase change upon a change in pH include cellulose acetate phthalate latex and cross-linked poly acrylic or other carbomer derivatives (e.g., Polycarbophil® and Carbopol®).

As yet another example, the droplet may be caused to undergo a phase change by reaction with a chemical reagent, for example, a crosslinking reagent. For example, a polymer contained within a liquid can be crosslinked, thereby turning the liquid into a solid or a gel state by crosslinking the chains of the polymer together. In some instances, a crosslinking reaction may be initiated by heat, pressure, or electromagnetic radiation. In certain cases, a crosslinking agent will be used to rigidify a droplet. Addition of a cleaving reagent may cause the rigidified droplet to be fluidized (e.g., the cleaving agent will cause the crosslinks that formed during crosslinking to be cleaved). Examples of rigidified droplets that may be prepared using crosslinking reagents are discussed more herein.

In some embodiments, a rigidified droplet may be a gel droplet (e.g., a droplet comprising or consisting essentially of a gel). As used herein, the term "gel" is given its ordinary meaning in the art and refers to a material comprising a polymer network that is able to trap and contain fluids. For example, a rigidified droplet may contain fluid from the fluidic droplet prior to rigidification of the fluidic droplet. The gel may comprise polymer chains that are crosslinked. The degree of crosslinking may be varied, in some cases, to tailor the extent to which the gel absorbs or retains fluids. Those of ordinary skill in the art will be able to select appropriate materials suitable for use as gels. In some cases, a gel may be formed from a gel precursor. For instance, the gel precursor may comprise a material that forms a gel upon reaction with another material (e.g., a photoinitiator or crosslinker). An example of a gel precursor includes polyacrylamide. In another embodiment, the gel precursor comprises a material that forms a gel upon application of electromagnetic radiation to the material, such as chitosan or poly(ethylene) glycol.

In some cases, a gel may be altered to form a fluidized state, e.g., a fluidic droplet. For instance, a polymer droplet may be fluidized by cleaving the crosslinks formed in the gel. Different types of gels and gel precursors that can be used in accordance with the present invention are described in more detail below.

In some embodiment, the gel is a natural gel; that is, a biologically-derived gel. A natural gel may include, for example, agarose (e.g., low melting point agarose), collagen, fibrin, laminin, Matrigel, alginate, and combinations thereof. In one particular embodiment, agarose is used. Droplets comprising natural gels and gel precursors, in some instances, may be rigidified or fluidized by a change in the temperature or pH of the droplet, etc.

Non-limiting examples of materials capable of forming gels from a liquid precursor include, but are not limited to, silicon-containing polymers, polyacrylamides (e.g., poly(N-isopropylacrylamide)), crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. Those of ordinary skill in the art can choose appropriate polymers that can be crosslinked, as well as suitable methods of crosslinking, based upon general knowledge of the art in combination with the description herein.

In some embodiments, a gel droplet may comprise a sol-gel. The term "sol-gel" as used herein means a gel derived from a sol, either by polymerizing the sol into an interconnected solid matrix, or by destabilizing the individual particles of a colloidal sol by means of an external agent. In general, the sol-gel process involves the change of a colloidal suspension system into a gel phase exhibiting a significantly higher viscosity. In some cases, the first liquid may comprise a sol-gel precursor comprising a mixture of solid particles (e.g., inorganic salts) suspended in a liquid, where a series of reactions including hydrolysis and polymerization reactions may be performed to form a rigidified droplet (e.g., a colloidal suspension). A non-limiting example of a sol-gel is silica xerogel. In some cases, the gel may be an organogel, where the polymer may be swollen by addition of an organic solvent.

A variety of definitions are now provided which will aid in understanding various aspects of the invention. Following, and interspersed with these definitions, is further disclosure that will more fully describe the invention.

A "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located. The diameter of a droplet, in a non-spherical droplet, is the diameter of a perfect mathematical sphere having the same volume as the non-spherical droplet. The fluidic droplets may be created using any suitable technique.

In some embodiments, a plurality of droplets may be prepared using microfluidic techniques, such as those disclosed in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be substantially miscible or substantially immiscible. In some cases, two fluids can be selected to be substantially immiscible within the time frame of formation of a stream of fluids, or within the time frame of reaction or interaction. In instances where the portions remain liquid for a significant period of time then the fluids should be substantially immiscible. In instances where, after contact and/or formation, the dispersed portions are rigidified, the fluids may need not be substantially immiscible. Those of ordinary skill in the art can select suitable substantially miscible or substantially immiscible fluids, using contact angle measurements or the like, to carry out the techniques of the invention.

As used herein, a first entity is "surrounded" by a second entity if a closed loop can be drawn around the first entity through only the second entity. A first entity is "completely surrounded" if closed loops going through only the second entity can be drawn around the first entity regardless of direction. A first entity is "substantially surrounded" if the loops going through only the second entity can be drawn around the first entity depending on the direction (e.g., in some cases, a loop around the first entity will comprise mostly of the second entity by may also comprise a third entity, or a fourth entity, etc.) In some aspect of the invention, the entities can both be fluids. For example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc.

A method of the present in invention may provide a plurality of droplets. In some embodiments, the plurality of droplets contain a first fluid and are substantially surrounded by a second fluid. In most, but not all embodiments, the first fluid and the second fluid are substantially immiscible. In some cases, however, the first and second fluids may be miscible. In some, but not all embodiments, the plurality of the droplets may be produced using microfluidic techniques, as discussed more herein. "Microfluidic," as used herein, refers to a device, apparatus or system including at least one fluid channel having a cross-sectional dimension of less than 1 mm, and a ratio of length to largest cross-sectional dimension of at least about 3:1.

As discussed herein, droplets produced using a microfluidic device may allow for the production of a plurality of droplets which have substantially the same composition. As used herein "substantially the same composition" refers to at least two droplets which comprise essentially the same material (e.g., fluid, polymer, gel, etc.). In some cases, two droplets which have substantially the same composition differ in their composition by no more than about 0.5%, no more than about 1%, no more than about 2%, no more than about 3%, no more than about 4%, no more than about 5%, no more than about 10%, no more than about 20%, and the like. Two droplets which have substantially the same composition may only differ in their composition because they contain distinguishable species. For example, the first droplet may comprise of a first fluid and contain internally at least one first species and the second droplets may comprise the same first fluid and contain internally at least one second species, where the first species and the second species are distinguishable with respect to each other. That is, the droplet comprise the same material (e.g., they are both formed of the same fluid, polymer, gel, etc.) but they each comprise at least one distinguishable species with respect to the other species.

The plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The "average diameter" of a population of droplets, as used herein, is the arithmetic average of the diameters of the droplets. Those of ordinary skill in the art will be able to determine the average diameter of a population of droplets, for example, using laser light scattering or other known techniques. As non-limiting examples, the average diameter of a droplet may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet may also be at least about 1 micrometer, at least about 2 micrometers, at least about 3 micrometers, at least about 5 micrometers, at least about 10 micrometers, at least about 15 micrometers, or at least about 20 micrometers in certain cases.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria. As mentioned above, a plurality of droplets of the present invention may be produced using microfluidic techniques. A benefit of using a plurality of droplets prepared using microfluidic techniques to prepare a plurality of fluidized or rigidified droplets comprising species is that the droplets, in most cases, will be monodisperse. Therefore, the properties of the droplets (e.g., size, shape, composition) of a first droplet in the suspension comprising a first type of species should be substantially similar to a second droplet in the suspension comprising a second type of species (with the exception of the distinguishing species). The monodisperse property of this technique may be difficult to achieve using other techniques, for example, producing a first and a second droplet comprising a first and a second species, respectively, directly from a microfluidic instrument (as opposed to the addition of the species after formation of a plurality of substantially similar droplets).

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. Examples of embodiments in which two or more droplets are fused have been described above. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square, or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5:1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic Droplets Encapsulated in Particles Such as Colloidal Particles," published as WO 2006/078841 on Jul. 27, 2006, each incorporated herein by reference.

The term "determining," as used herein, generally refers to the analysis or measurement of a target analyte molecule, for example, quantitatively or qualitatively, or the detection of the presence or absence of a target analyte molecule. "Determining" may also refer to the analysis or measurement of an interaction between at least one species and a target analyte molecule, for example, quantitatively or qualitatively, or by detecting the presence or absence of the interaction. Example techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

In one embodiment, a kit may be provided, containing one or more of the above compositions. A "kit," as used herein, typically defines a package or an assembly including one or more of the compositions of the invention, and/or other compositions associated with the invention, for example, as previously described. Each of the compositions of the kit may be provided in liquid form (e.g., in solution), in solid form (e.g., a dried powder), etc. A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

Incorporated herein by reference is a U.S. Provisional Patent Application Ser. No. 61/098,674, filed Sep. 19, 2008, entitled "Creation of Libraries of Droplets and Related Species," by Weitz, et al., U.S. Provisional Patent Application Ser. No. 61/008,862, filed Dec. 21, 2007, entitled "Systems and Methods for Nucleic Acid Sequencing," by Weitz, et al., U.S. Provisional Patent Application Ser. No. 61/098,710, filed Sep. 19, 2008, entitled "Systems and Methods for Nucleic Acid Sequencing," by Weitz, et al., and International Patent Application No. PCT/US2008/013912, filed Dec. 19, 2008, entitled "Systems and Methods for Nucleic Acid Sequencing," by Weitz, et al.

The following examples are intended to illustrate certain embodiments of the present invention, but do not exemplify the full scope of the invention.

Example 1

The following example describes the formation of a plurality of rigidified droplets comprising a first group of rigidified droplets comprising a first species and a second group of rigidified droplets comprising a second species, wherein the first species and the second species are distinguishable from each other, according to one embodiment of the present invention.

Figure 9A:
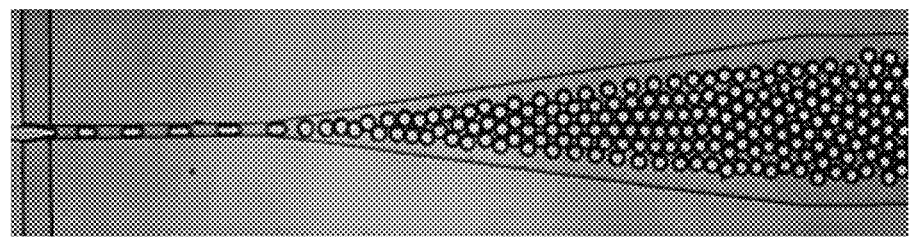
FIG. 9A shows the formation of a plurality of droplets comprising DNA oligonucleotides, according to one embodiment.
Figure 9B:
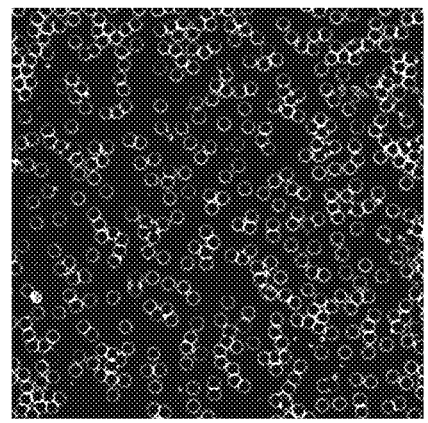
FIG. 9B shows the plurality of droplets formed in FIG. 9A following rigidification and exposure to water, according to one embodiment.

A plurality of rigidified droplets were formed using microfluidic techniques as follows. A solution comprising water, 5% acrylamide, 0.25% bisacrylamide, 0.1% ammonium persulfate, and 1 uM of a first acrydite-labeled DNA oligonucleotide 20-mer was flowed through the center channel of a microfluidic device and focused by oil containing 0.1% TEMED in the side channels through a 10 micron nozzle to produce approximately 12 micron pre-gel droplets, as depicted in FIG. 9A. The droplets were allowed to rigidify for 30 minutes at 50° C. via polymerization reactions. FIG. 9B shows the plurality of rigidified droplets after being exposed to water.

Figure 9C:
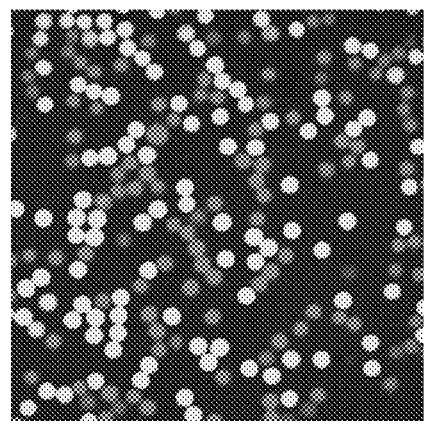
FIG. 9C shows a fluorescent microscope image of a first group or rigidified droplets comprising a first DNA oligonucleotide and a second group of rigidified droplets comprising a second DNA oligoncleotide, respectively, and which have been visualized by exposure to a two distinguishable labeled oligonucleotides, according to one embodiment of the present invention.

The above steps (e.g., FIGS. 9A and 9B) were repeated for a second group of droplets comprising a second acrydite-labeled DNA oligonucleotide 20-mer that was distinguishable from the first DNA oligonucleotide 20-mer. A suspension of droplets was formed comprising some of the first group and the second group of rigidified droplets. The suspension of rigidified droplets was exposed to a plurality of a first type and a second type distinguishably labeled oligonucleotide specific to the first DNA oligonucleotide and the second DNA oligonucleotide, respectively. The distinguishably labeled oligonucleotides hybridized to the specified DNA in the rigidified droplets. FIG. 9C shows a fluorescence microscope image of the rigidified droplets following hybridization wherein one type of rigidified droplets is shown in grey and the other type is shown in white.

While several embodiments of the invention have been described and illustrated herein, those of ordinary skill in the art will readily envision a variety of other means and/or structures for performing the functions and/or obtaining the results and/or one or more of the advantages described herein, and each of such variations or modifications is deemed to be within the scope of the present invention. More generally, those skilled in the art will readily appreciate that all parameters, dimensions, materials, and configurations described herein are meant to be exemplary and that the actual parameters, dimensions, materials, and configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and/or claimed. The present invention is directed to each individual feature, system, material and/or method described herein. In addition, any combination of two or more such features, systems, articles, materials and/or methods, if such features, systems, articles, materials and/or methods are not mutually inconsistent, is included within the scope of the present invention.

All definitions as used herein are solely for the purposes of this disclosure. These definitions should not necessarily be imputed to other commonly-owned patents and/or patent applications, whether related or unrelated to this disclosure. The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

What is claimed is:

1. A method of forming a suspension of droplets in a fluid, the method comprising:
   providing a suspension comprising a plurality of fluidic droplets suspended in a second fluid, each of the fluidic droplets comprising a first fluid and a gel droplet capable of undergoing a phase change in response to an environmental change, each of the gel droplets having substantially the same composition as the other gel droplets but containing a droplet-specific distinguishable species of nucleic acid probes with respect to each of the other gel droplets based on different nucleic acid sequences in the distinguishable species,
   wherein each of the plurality of fluidic droplets comprises a target that did not originate from the gel droplet and interacts with the distinguishable species of nucleic acid probes upon fluidization of the gel droplets and release of the distinguishable species therein,
   wherein the first fluid and the second fluid are substantially immiscible; and
   fluidizing at least some of the gel droplets to release the distinguishable species therein and form a plurality of fluidized droplets containing distinguishable species and suspended within the second fluid by exposing the gel droplets to the environmental change at least sufficiently to fluidize at least some of the gel droplets, wherein the plurality of fluidized droplets are substantially immiscible in the second fluid.

2. The method of claim 1, wherein the gel droplets are formed using microfluidic techniques.

3. The method of claim 1, wherein the first fluid is hydrophilic and the second fluid is hydrophobic.

4. The method of claim 1, wherein the first fluid is hydrophobic and the second fluid is hydrophilic.

5. The method of claim 1, wherein the plurality of fluidic droplets comprises substantially the same composition.

6. The method of claim 1, wherein the environmental change comprises a change in temperature and the temperature of the gel droplets is raised by about 10° C.

7. The method of claim 1, wherein the environmental change comprises a change in temperature and the temperature of the gel droplets is raised by about 20° C.

8. The method of claim 1, further comprising fusing at least some of the plurality of fluidic droplets.

9. The method of claim 1, wherein the target is a nucleic acid.

10. The method of claim 9, wherein the target is a nucleic acid isolated from a cell.

11. The method of claim 9, further comprising the step of determining the sequence of the nucleic acid.

12. The method of claim 1, wherein at least about 5 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

13. The method of claim 1, wherein at least about 10 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

14. The method of claim 1, wherein at least about 20 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

15. The method of claim 1, wherein at least about 64 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

16. The method of claim 1, wherein at least about 100 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

17. The method of claim 1, wherein at least about 4096 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

18. The method of claim 1, wherein at least about 10,000 groups of gel droplets are provided with each of the gel droplets having substantially the same composition as the other gel droplets but containing a distinguishable species of nucleic acid probes with respect to each of the other gel droplets based on different nucleic acid sequences in the distinguishable species.

19. The method of claim 1, wherein the gel droplets have a distribution of average diameters such that no more than about 10% of the droplets have an average diameter that deviates greater than about 10% of the average diameter.

20. The method of claim 1 wherein the plurality of fluidic droplets has a distribution of average diameters such that no more than about 10% of the droplets have an average diameter that deviates greater than about 10% of the average diameter.

21. The method of claim 1, wherein the gel droplets comprise agarose.

22. The method of claim 1, wherein at least some of the distinguishable species are immobilized to gel within the gel droplets.

23. The method of claim 1, wherein the target is a cell.

* * * * *